(12) United States Patent
Rulkov et al.

(10) Patent No.: US 12,178,565 B2
(45) Date of Patent: Dec. 31, 2024

(54) SYSTEMS AND METHODS FOR IMAGING A BODY REGION USING IMPLANTED MARKERS

(71) Applicant: Cianna Medical, Inc., Aliso Viejo, CA (US)

(72) Inventors: Nikolai Rulkov, San Diego, CA (US); John E. Greene, Valley Center, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 1016 days.

(21) Appl. No.: 17/089,440

(22) Filed: Nov. 4, 2020

(65) Prior Publication Data

US 2021/0128012 A1 May 6, 2021

Related U.S. Application Data

(60) Provisional application No. 62/931,059, filed on Nov. 5, 2019.

(51) Int. Cl.
 *A61B 5/06* (2006.01)
 *A61B 5/00* (2006.01)
 (Continued)

(52) U.S. Cl.
 CPC ............ *A61B 5/064* (2013.01); *A61B 5/0004* (2013.01); *A61B 5/0084* (2013.01); *A61B 5/05* (2013.01);
 (Continued)

(58) Field of Classification Search
 None
 See application file for complete search history.

(56) References Cited

U.S. PATENT DOCUMENTS

| | | |
|---|---|---|
| 5,190,059 A | 3/1993 | Fabian et al. |
| 5,320,098 A | 6/1994 | Davidson |

(Continued)

FOREIGN PATENT DOCUMENTS

| | | |
|---|---|---|
| CN | 108348190 A | 7/2018 |
| EP | 1374793 | 2/2004 |

(Continued)

OTHER PUBLICATIONS

Office Action dated Jun. 9, 2022 for U.S. Appl. No. 17/089,437.
(Continued)

*Primary Examiner* — Katherine L Fernandez
(74) *Attorney, Agent, or Firm* — Dorsey & Whitney LLP

(57) ABSTRACT

Apparatus, systems, and methods are provided for localization of a region within a patient's body using markers implanted within the region. In an exemplary embodiment, a probe includes a distal end for placement against a surface of the region; one or more antennas for transmitting electromagnetic signals into and receiving reflected signals from the region; a light source for delivering light pulses into the region whereupon the markers modulate reflected signals. A processor of the probe processes the modulated reflected signals at one or more of the surface locations to determine marker locations within the region to obtain a reference frame, determine distance values corresponding to distances from the respective markers to the distal end at each of the surface locations, and determine coordinates of the surface locations relative to the reference frame to generate a three dimensional model of the body region.

10 Claims, 23 Drawing Sheets

(51) Int. Cl.
    *A61B 5/05*          (2021.01)
    *A61B 90/00*        (2016.01)
    *G01S 13/02*        (2006.01)
    *G01S 13/08*        (2006.01)

(52) U.S. Cl.
    CPC ............ *A61B 5/6867* (2013.01); *A61B 5/742* (2013.01); *A61B 90/37* (2016.02); *A61B 90/39* (2016.02); *G01S 13/0209* (2013.01); *G01S 13/08* (2013.01); *A61B 2090/3908* (2016.02); *A61B 2090/3975* (2016.02); *A61B 2090/3987* (2016.02)

(56) References Cited

U.S. PATENT DOCUMENTS

| | | |
|---|---|---|
| 5,361,070 A | 11/1994 | McEwan |
| 5,387,259 A | 2/1995 | Davidson |
| 5,573,012 A | 11/1996 | McEwan |
| 5,764,162 A | 6/1998 | Ehrlich |
| 5,766,208 A | 6/1998 | McEwan |
| 5,853,366 A | 12/1998 | Dowlatshahi |
| 5,879,357 A | 3/1999 | Heaton et al. |
| 6,061,589 A | 5/2000 | Bridges et al. |
| 6,127,940 A | 10/2000 | Weinberg |
| 6,144,300 A | 11/2000 | Dames |
| 6,226,548 B1 | 5/2001 | Foley |
| 6,233,479 B1 | 5/2001 | Haddad et al. |
| 6,363,940 B1 | 4/2002 | Krag |
| 6,492,933 B1 | 12/2002 | McEwan |
| 6,496,717 B2 | 12/2002 | Cox et al. |
| 6,575,991 B1 | 6/2003 | Chesbrough et al. |
| 6,725,083 B1 | 4/2004 | Burbank et al. |
| 6,898,464 B2 | 5/2005 | Edell |
| 6,914,552 B1 | 7/2005 | McEwan |
| 7,075,968 B1 | 7/2006 | Ghassemzadeh et al. |
| 7,174,201 B2 | 2/2007 | Govari et al. |
| 7,567,200 B1 | 7/2009 | Osterweil |
| 7,569,065 B2 | 8/2009 | Chesbrough et al. |
| 7,881,030 B1 | 2/2011 | Li |
| 8,052,708 B2 | 11/2011 | Chesbrough et al. |
| 9,136,690 B1 | 9/2015 | Upadhyaya |
| 9,713,437 B2 | 7/2017 | Fullerton |
| 9,987,097 B2 | 6/2018 | Van Der Weide |
| 10,383,544 B2 | 8/2019 | Fullerton et al. |
| 10,499,832 B2 | 12/2019 | Greene et al. |
| 10,610,326 B2 | 4/2020 | Rulkov et al. |
| 10,660,542 B2 | 5/2020 | Greene et al. |
| 10,786,310 B2* | 9/2020 | Bharat .................. A61B 5/062 |
| 2003/0004411 A1 | 1/2003 | Govari et al. |
| 2003/0006906 A1 | 1/2003 | Gardner et al. |
| 2003/0018246 A1 | 1/2003 | Govari et al. |
| 2003/0036713 A1 | 2/2003 | Bouton et al. |
| 2003/0088186 A1 | 5/2003 | Doody |
| 2003/0192557 A1 | 10/2003 | Krag et al. |
| 2004/0054385 A1 | 3/2004 | Lesho |
| 2005/0036945 A1 | 2/2005 | Thomas |
| 2005/0059884 A1 | 3/2005 | Krag |
| 2005/0096589 A1 | 5/2005 | Shachar |
| 2005/0151650 A1 | 7/2005 | Wright et al. |
| 2005/0163336 A1 | 7/2005 | Hiramoto |
| 2006/0025795 A1 | 2/2006 | Chesbrough et al. |
| 2006/0256981 A1 | 11/2006 | Song |
| 2006/0258933 A1 | 11/2006 | Ellis et al. |
| 2007/0027505 A1 | 2/2007 | Ginggen |
| 2007/0038014 A1 | 2/2007 | Cox et al. |
| 2007/0093726 A1 | 4/2007 | Leopold et al. |
| 2007/0100666 A1 | 5/2007 | Stivoric |
| 2007/0135711 A1 | 6/2007 | Chernomorsky |
| 2007/0195929 A1 | 8/2007 | Ruchala |
| 2007/0243225 A1 | 10/2007 | McKay |
| 2008/0027313 A1 | 1/2008 | Shachar |
| 2008/0071169 A1 | 3/2008 | Craddock et al. |
| 2008/0086046 A1 | 4/2008 | Petcavich et al. |
| 2008/0183068 A1 | 7/2008 | Carls et al. |
| 2008/0200802 A1 | 8/2008 | Bhavaraju et al. |
| 2008/0269601 A1 | 10/2008 | Shewamb |
| 2008/0281190 A1 | 11/2008 | Petcavich et al. |
| 2009/0015832 A1 | 1/2009 | Popovic et al. |
| 2009/0157068 A1 | 6/2009 | Kallel et al. |
| 2009/0216115 A1 | 8/2009 | Seiler |
| 2009/0248014 A1 | 10/2009 | Shachar et al. |
| 2009/0281422 A1 | 11/2009 | Salama et al. |
| 2009/0292174 A1 | 11/2009 | Shigemori |
| 2009/0299174 A1 | 12/2009 | Wright et al. |
| 2010/0004523 A1 | 1/2010 | August et al. |
| 2010/0234792 A1 | 9/2010 | Dacey |
| 2010/0262013 A1 | 10/2010 | Smith et al. |
| 2010/0275934 A1 | 11/2010 | Keren |
| 2011/0080678 A1 | 4/2011 | Zhao |
| 2011/0166442 A1 | 7/2011 | Sarvazyan |
| 2011/0313288 A1 | 12/2011 | Chi Sing et al. |
| 2012/0212380 A1 | 8/2012 | Theobold et al. |
| 2013/0006120 A1 | 1/2013 | Druse et al. |
| 2013/0310680 A1* | 11/2013 | Werahera ............. A61B 5/0035 600/478 |
| 2014/0308522 A1 | 10/2014 | Wu et al. |
| 2014/0309522 A1* | 10/2014 | Fullerton ............... A61B 90/39 600/424 |
| 2014/0327048 A1 | 11/2014 | Chow et al. |
| 2015/0049907 A1 | 2/2015 | Hong et al. |
| 2015/0349150 A1 | 12/2015 | Carey et al. |
| 2016/0294056 A1 | 10/2016 | Manteghi et al. |
| 2017/0007352 A1 | 1/2017 | King et al. |
| 2017/0042622 A1 | 2/2017 | Yang |
| 2017/0095315 A1* | 4/2017 | van der Weide .. A61B 18/1402 |
| 2017/0319102 A1 | 11/2017 | Greene et al. |
| 2018/0035914 A1 | 2/2018 | Fullerton et al. |
| 2019/0307632 A1 | 10/2019 | Yashiro et al. |
| 2019/0365279 A1 | 12/2019 | Fullerton et al. |
| 2020/0077922 A1 | 3/2020 | Greene et al. |
| 2020/0170541 A1 | 6/2020 | Greene et al. |
| 2020/0264298 A1 | 8/2020 | Haseltine et al. |
| 2020/0390364 A1 | 12/2020 | Greene et al. |
| 2020/0390516 A1 | 12/2020 | Rulkov et al. |
| 2021/0068705 A1 | 3/2021 | Greene et al. |
| 2021/0128268 A1 | 5/2021 | Rulkov et al. |
| 2022/0015859 A1 | 1/2022 | Van Der Weide et al. |

FOREIGN PATENT DOCUMENTS

| | | |
|---|---|---|
| EP | 1510183 | 3/2005 |
| JP | 2005536314 | 12/2005 |
| JP | 2009273610 | 11/2009 |
| JP | 2012178525 | 9/2012 |
| JP | 2012182381 | 9/2012 |
| JP | 2013098222 | 5/2013 |
| JP | 2014033055 | 2/2014 |
| WO | 2001016554 | 3/2001 |
| WO | 200239918 | 5/2002 |
| WO | 2004030552 | 4/2004 |
| WO | 2004032779 | 4/2004 |
| WO | 2007087447 | 8/2007 |
| WO | 2007117478 | 10/2007 |
| WO | 2014149183 | 9/2014 |
| WO | 2016197008 | 12/2016 |
| WO | 2016197008 A1 | 12/2016 |

OTHER PUBLICATIONS

Office Action dated Jun. 22, 2023 for U.S. Appl. No. 17/089,437.
International Search Report and Written Opinion dated Feb. 26, 2021 for PCT/US2020/058912.
Heimann, et al., A Comparison of Three Dimensional Ultrasound, Clips and CT for Measuring Interfractional Breast Lumpectomy Cavity Motion, Journal of Nuclear Medicine and Radiation Therapy, vol. 7 No. 2 ,Feb. 2016 ,1-8.
European Search Report dated Nov. 22, 2023 for EP20886275.9.
European Examination Report dated Aug. 27, 2021 for EP17722535.6.
European Search Report dated Mar. 4, 2021 for EP16732061.3.
International Search Report and Written Opinion dated Jan. 3, 2020 for PCT/US2019/049583.

(56) References Cited

OTHER PUBLICATIONS

International Search Report and Written Opinion dated May 24, 2017 for PCT/US2017/020260.
International Search Report and Written Opinion dated May 28, 2015 for PCT/US2014/013239.
International Search Report and Written Opinion dated Sep. 20, 2018 for PCT/US2018/035219.
International Search Report and Written Opinion dated Oct. 25, 2016 for PCT/US2016/035846.
Notice of Allowance dated Apr. 8, 2020 for U.S. Appl. No. 15/993,559.
Notice of Allowance dated May 6, 2020 for U.S. Appl. No. 15/928,085.
Notice of Allowance dated Jun. 19, 2020 for U.S. Appl. No. 15/928,085.
Notice of Allowance dated Aug. 23, 2021 for U.S. Appl. No. 16/708,286.
Notice of Allowance dated Oct. 24, 2019 for U.S. Appl. No. 14/934,019.
Notice of Allowance dated Nov. 29, 2021 for U.S. Appl. No. 16/544,765.
Office Action dated Jan. 21, 2020 for U.S. Appl. No. 15/928,085.
Office Action dated Mar. 19, 2020 for U.S. Appl. No. 15/446,944.
Office Action dated Apr. 24, 2019 for U.S. Appl. No. 14/934,019.
Office Action dated May 18, 2021 for U.S. Appl. No. 16/708,286.
Office Action dated Jun. 17, 2021 for U.S. Appl. No. 16/124,053.
Office Action dated Aug. 13, 2021 for U.S. Appl. No. 16/544,765.
Office Action dated Sep. 23, 2021 for U.S. Appl. No. 16/841,417.
Office Action dated Oct. 7, 2019 for U.S. Appl. No. 14/934,019.
Office Action dated Nov. 27, 2019 for U.S. Appl. No. 15/993,559.
http://www.theradarreflectorsite.org.WebManuscript;, Chapter 6: Passive Radar Reflector Elements; accessed on Mar. 12, 2020 ,64-81.
Ahmadian, et al., Miniture Transmittter for Implantable Micro Systems, Proceedings of the 25th Annual International Conference of the IEEE EMBS, Cancun Mexico ,Sep. 17-21, 2003.
Azevedo, et al., Micropower Impluse Radar, Science & Technology Review ,Jan./Feb. 1996 ,7 pgs.
Hagness, et al., Three-Dimensional FDTD Analysis of a Pulsed Microwave Confocal System for Breast Cancer Detection, IEEE Transaction on Antennas and Propagation, vol. 47 No. 5 ,May 1999 ,9 pgs.
Hilger, et al., ultraMEDIS—Ultra-Wideband Sensing in Medicine, Intech ,2013 ,66 pgs.
Hughes, et al., A Multi-Site Validation Trial of Radioactive Seed Localization as an Alternative to Wire Localization, The Breast Journal, vol. 14 No. 2, Blackwell Publishing Inc. ,2008 ,5 pgs.
Krishnan, et al., UWB-IR Active Reflector for High Precision Ranging and Positioning Applications, Institute of Infocomm Research, A Star Singapore, IEEE ,2010 ,14-18.
Nilavalan, et al., Wideband Microstrip Patch Antenna Design for Breast Cancer Tumor Detection, IEEE Xplore/IEEE.org, Institution of Engineering and Technology ,Apr. 30, 2007 ,1 pg.
Shannon, et al., Dialectric-Filled Slotline Bowtie Antenna for Breast Cancer Detection, Electronics Letters, 31, vol. 41 No. 7 ,Mar. 2005 ,2 pgs.
Stephan, et al., Wire Localization Procedure—Breast Biopsy of Lumpectomy, About.com/Breast Cancer, American Cancer Society/Ohio State Medical Center ,Sep. 8, 2008 ,2 pgs.
Xing Yun, et al., Broadband Cross-Polarized Bowtie Antenna for Breast Cancer Detection, Department of Electrical and Computer Engineering, University of Calgary Calgary, Alberta, Canada T2N 1N4 ,Jun. 22-27, 2003 ,1091-1094.
Yun, et al., Broadband Cross-Polarized bowtie Antenna, Department of Electrical and Computer Engineering, University of Calgary, Calgary, Alberta, CA, IEEE ,2003 ,1091-1094.
European Search Report dated Apr. 6, 2021 for EP20203175.3.
Office Action dated Jan. 20, 2023 for U.S. Appl. No. 17/089,437.
Office Action dated Feb. 14, 2022 for U.S. Appl. No. 16/881,893.
Office Action dated Dec. 20, 2021 for U.S. Appl. No. 16/124,053.
Office Action dated Dec. 21, 2021 for U.S. Appl. No. 17/093,464.
Azevedo, et al., "Micropower Impluse Radar", Science & Technology Review, 7 pgs, 1996.
Hagness, et al., "Three-Dimensional FDTD Analysis of a Pulsed Microwave Confocal System for Breast Cancer Detection", IEEE Transaction on Antennas and Propagation, vol. 47 No. 5, May 1, 1999, 9 pgs.
Hilger, et al., "ultraMEDIS—Ultra-Wideband Sensing in Medicine", Intech, Jan. 1, 2013, 66 pgs.
Hughes, et al., "A Multi-Site Validation Trial of Radioactive Seed Localization as an Alternative to Wire Localization", The Breast Journal, vol. 14 No. 2, Blackwell Publishing Inc., Jan. 1, 2008, 5 pgs.
Krishnan, et al., "UWB-IR Active Reflector for High Precision Ranging and Positioning Applications", Institute of Infocomm Research, A Star Singapore, IEEE, Jan. 1, 2010, 14-18.
Shannon, et al., "Dialectric-Filled Slotline Bowtie Antenna for Breast Cancer Detection", Electronics Letters, 31, vol. 41 No. 7, Mar. 1, 2005, 2 pgs.
Stephan, "Wire Localization Procedure—Breast Biopsy of Lumpectomy, About.com/Breast Cancer", American Cancer Society/Ohio State Medical Center, Sep. 8, 2008, 2 pgs.
Yun, et al., "Broadband Cross-Polarized bowtie Antenna", Department of Electrical and Computer Engineering, University of Calgary, Calgary, Alberta, CA, IEEE, Jan. 1, 2003, 1091-1094.
European Search Report dated Mar. 4, 2024 for EP23200866.4.
Office Action dated Feb. 1, 2024 for U.S. Appl. No. 17/089,437.
Krishnan, et al., "UWB-IR Active Reflector for High Precision Ranging and Positioning Applications", Institute of Inforcomm Research, A Star Singapore, IEEE, Nov. 17, 2010, 14-18.
Xing Yun, et al., "Broadband Cross-polarized Bowtie Antenna for Breast Cancer Detection", IEEE Antennas and Propagation Society International Symposium, vol. 3, Jun. 22, 2003, 1091-1094.
Notice of Allowance dated Aug. 14, 2024 for U.S. Appl. No. 17/089,437.

* cited by examiner

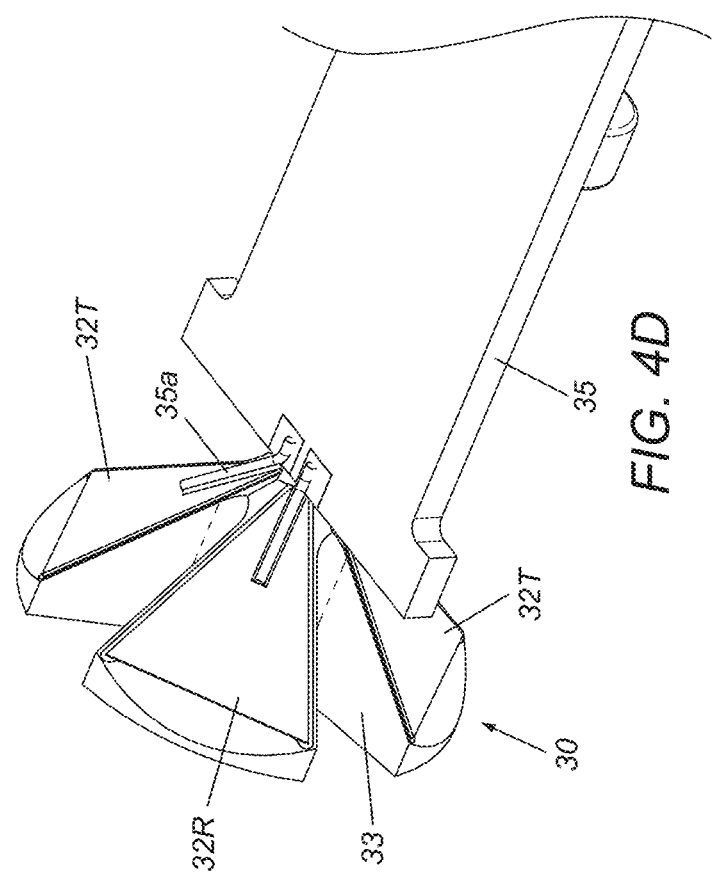
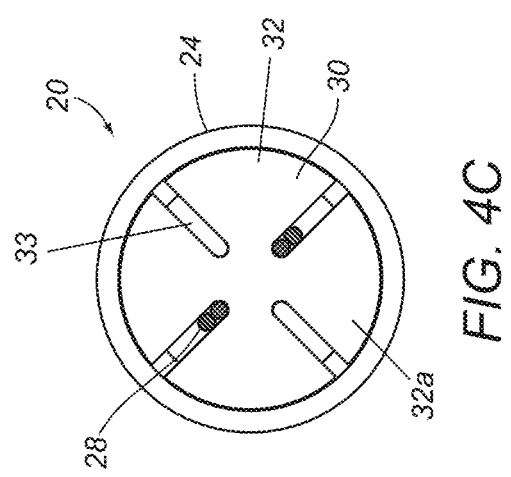

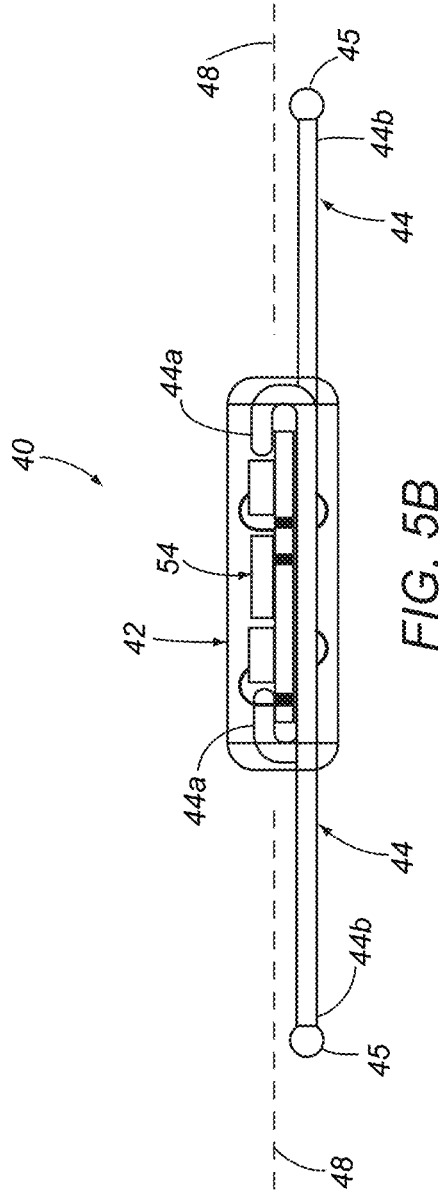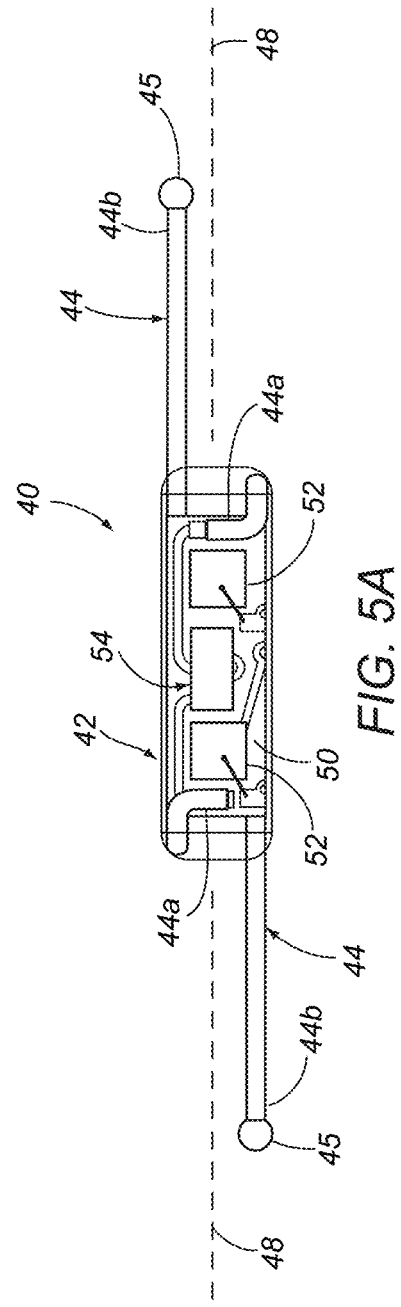

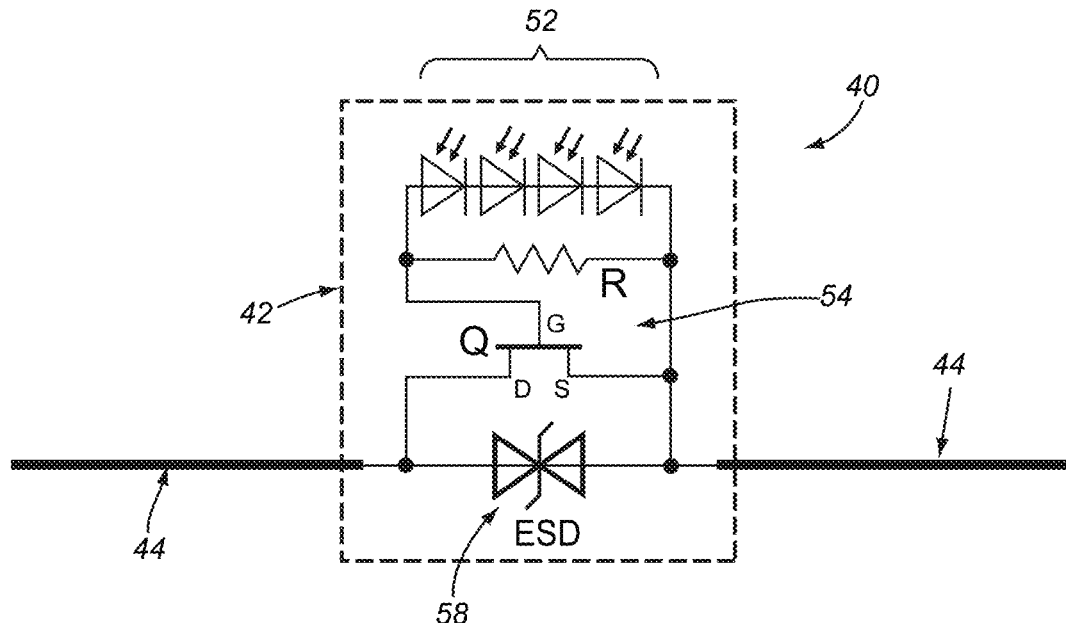
FIG. 6
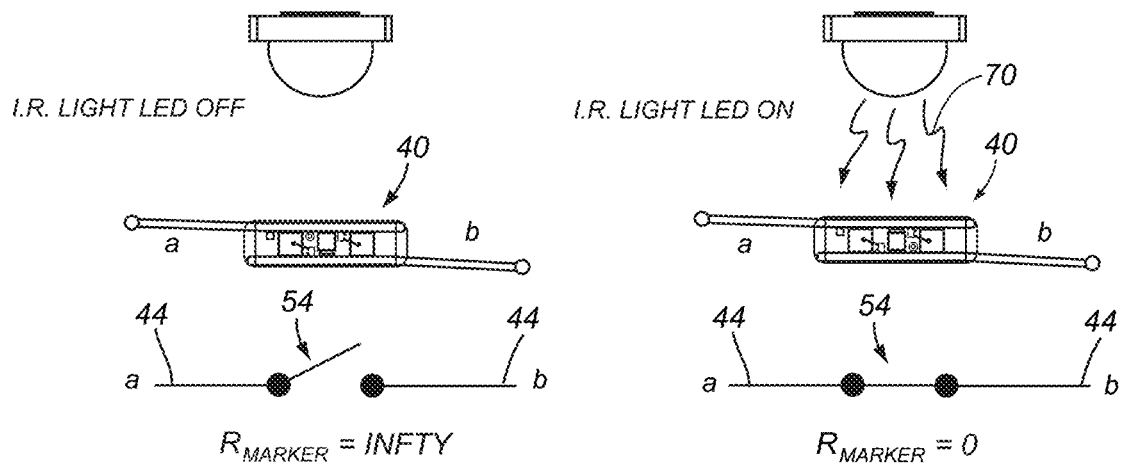
FIG. 7A
FIG. 7B

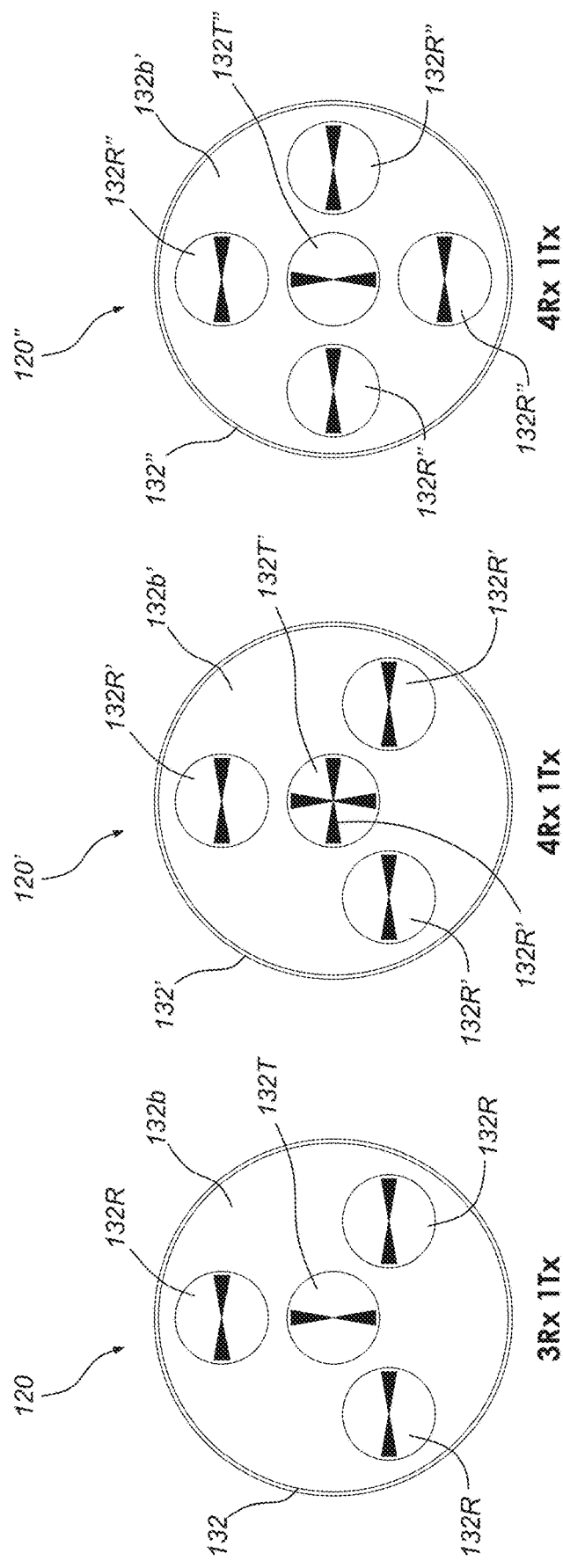

SYSTEMS AND METHODS FOR IMAGING A BODY REGION USING IMPLANTED MARKERS

RELATED APPLICATIONS

The present application claims priority to U.S. Provisional Application No. 62/931,059, filed on Nov. 5, 2019 and titled, "SYSTEMS AND METHODS FOR IMAGING A BODY REGION USING IMPLANTED MARKERS," which is hereby incorporated by reference in its entirety.

TECHNICAL FIELD

The present disclosure relates to systems and methods for imaging a region of a patient's body, e.g., by identifying and/or locating markers implanted within the patient's body to generate a model of the region, e.g., in anticipation of and/or during surgical or other medical procedures, such as during lumpectomy procedures.

BRIEF DESCRIPTION OF THE DRAWINGS

These and other features, aspects, and advantages of the present disclosure will become better understood with regard to the following description, appended claims, and accompanying drawings where:

FIGS. 4A-4C are perspective, side, and end views, respectively, of an exemplary probe that may be included in a system such that shown in FIGS. 1-2.

FIG. 4D is a detail of an antenna assembly that may be included in the probe shown in FIGS. 4A-4C.

FIGS. 5A and 5B are top and side views, respectively, of an exemplary embodiment of a marker for implantation within a patient's body.

FIG. 6 is an exemplary embodiment of a schematic of a circuit that may be included in the marker of FIGS. 5A and 5B.

FIGS. 7A and 7B are schematics demonstrating operation of a switch of the circuit of FIG. 6.

FIGS. 14A-14C show alternative configurations of an antenna assembly that may be included in the probe of FIGS. 13A and 13B.

DETAILED DESCRIPTION

Figure 1:
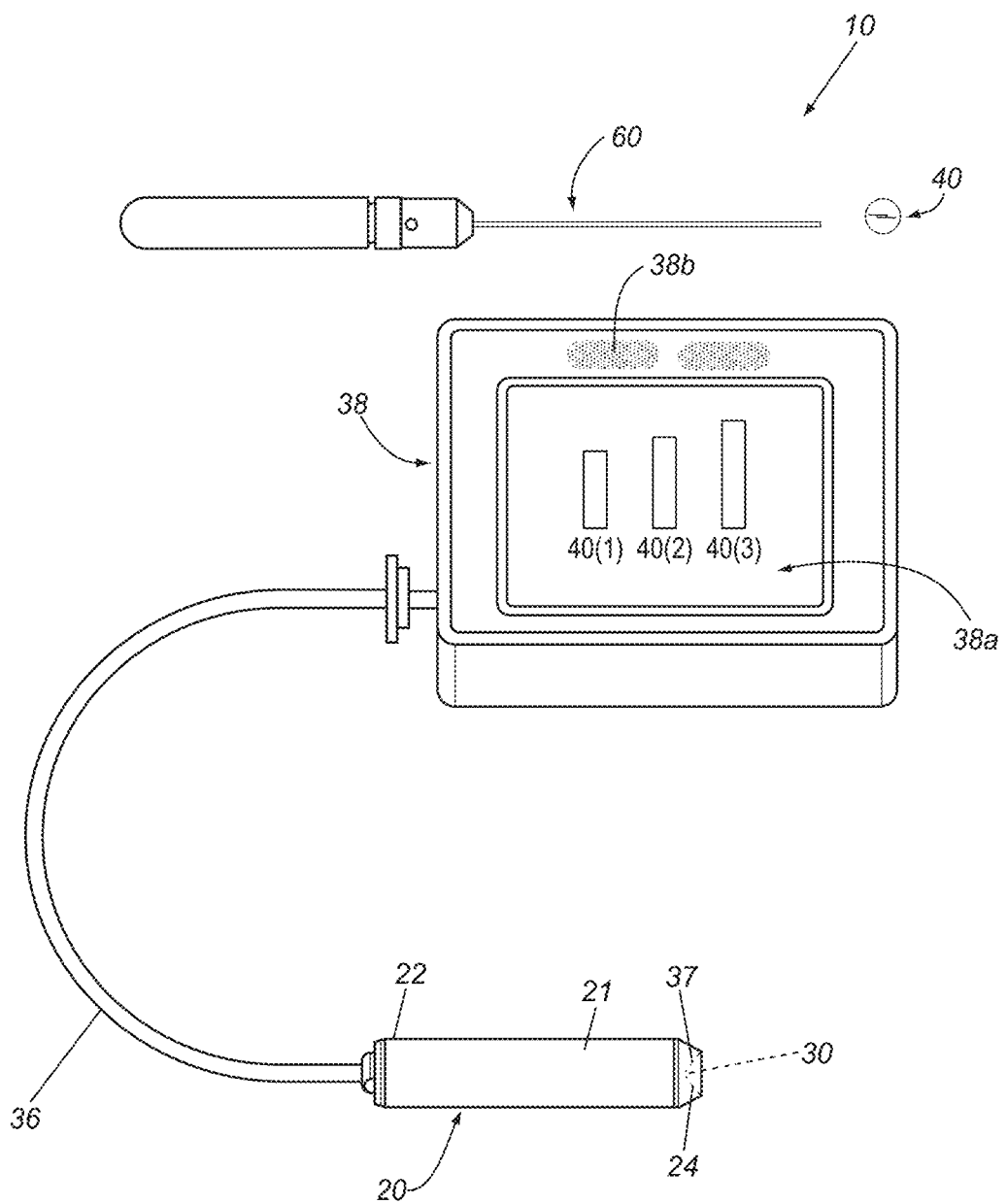
FIG. 1 shows an exemplary embodiment of a system for delivering and localizing a marker within a patient's body including a probe and a delivery device for implanting one or more markers within a patient's body.

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other body structures in advance of and/or during surgical, diagnostic, or other medical procedures would be useful.

Embodiments herein are directed to systems and methods for imaging a region of a patient's body, e.g., by identifying and/or locating markers implanted within the patient's body to generate a model of the region. For example, the systems and methods herein may be used to generate a three-dimensional model of a body region of a patient using a plurality of markers to obtain a reference frame, e.g., in anticipation of and/or during surgical or other medical procedures, such as during lumpectomy procedures.

In accordance with one embodiment, a probe is provided for localization of a region within a patient's body using a plurality of markers implanted within the region. The probe may include a housing including a distal end configured for placement against a surface of the region towards the markers, one or more antennas adjacent the distal end for transmitting electromagnetic signals into a patient's body and receiving reflected signals from the patient's body, and a light source for delivering light pulses into a patient's body synchronized with the electromagnetic signals whereupon the markers modulate reflected signals from the respective markers. In addition, a processor or controller of the probe is coupled to the one or more antennas and configured to process the modulated reflected signals from the markers at one or more of the surface locations to determine marker locations within the region to obtain a reference frame relative to the region; determine distance values corresponding to distances from the respective markers to the distal end at each of the surface locations; and determine coordinates of the surface locations relative to the reference frame to generate a model of the body region. The model may then be presented on a display, e.g., showing the markers within the body region, to facilitate a medical procedure.

In accordance with still another embodiment, a system is provided for a system is provided for localization of a region within a patient's body that includes a plurality of markers sized for implantation within a region within a patient's body and a probe. Each marker may include an energy converter configured to transform light pulses into electrical energy; one or more elongate members coupled to a switch to provide one or more antennas; and a circuit coupled to the energy converter and switch to open and close the switch to modulate electromagnetic signals reflected by the marker based at least in part on the light pulses. The probe may include a housing comprising a distal end configured for placement against a surface of the region towards the markers; one or more antennas adjacent the distal end for transmitting electromagnetic signals into a patient's body and receiving reflected signals from the patient's body; a light source for delivering light pulses into a patient's body synchronized with the electromagnetic signals whereupon the markers modulate reflected signals from the respective markers; and a processor coupled to the one or more antennas. The processor may be configured to process the modulated reflected signals from the markers at one or more of the surface locations to determine marker locations within the region to obtain a reference frame relative to the region; determine distance values corresponding to distances from the respective markers to the distal end at each of the surface locations; and determine coordinates of the surface locations relative to the reference frame to generate a model of the body region.

In accordance with still another embodiment, a method is provided for localization of a region within a patient's body using a plurality of markers implanted within the region that includes placing a distal end of a probe sequentially against a plurality of surface locations adjacent the region; at each of the surface locations, activating the probe to transmit electromagnetic signals into the patient's body, receive reflected signals from the patient's body, and in synchronization with transmitting the electromagnetic signals, deliver light pulses into the patient's body, whereupon the plurality of markers modulate reflected signals from the respective markers; and a processor of the probe processes the modulated reflected signals from one or more of the surface locations to determine marker locations within the region to obtain a reference frame relative to the region and to determine distance values corresponding to distances from the respective markers to the distal end at each of the surface locations, and the processor determines coordinates of the surface locations relative to the reference frame to generate a model of the region.

In accordance with yet another embodiment, a method is provided for localization of a region within a patient's body that includes implanting a plurality of markers within the region, e.g., to identify a lesion therein; placing a distal end of a probe sequentially against a plurality of surface locations adjacent the region; and at each of the surface locations, activating the probe to transmit electromagnetic signals into the patient's body, receive reflected signals from the patient's body, and in synchronization with transmitting the electromagnetic signals, deliver light pulses into the patient's body, whereupon the plurality of markers modulate reflected signals from the respective markers. A processor of the probe may process the modulated reflected signals from one or more of the surface locations to determine marker locations within the region to obtain a reference frame relative to the region and to determine distance values corresponding to distances from the respective markers to the distal end at each of the surface locations, and the processor may determine coordinates of the surface locations relative to the reference frame to generate a three dimensional model of the region.

In accordance with another embodiment, a probe is provided for localization of a region within a patient's body using one or more markers implanted within the region, the probe including a housing comprising a distal end including a substrate configured for placement against a surface of the region towards the markers; a transmit antenna on the substrate configured for transmitting electromagnetic signals into a patient's body; a plurality of receive antennas spaced apart from one another on the substrate, each configured for receiving reflected signals from the patient's body; a light source for delivering light pulses distally from the substrate into a patient's body synchronized with the electromagnetic signals whereupon the one or more markers modulate reflected signals from the one or more markers; and a processor coupled to the plurality of sets of receive antennas configured to process the modulated reflected signals from the one or more markers to determine distance values corresponding to distances from the one or more markers to respective sets of receive antennas, and determine coordinates defining the spatial location of the one or more markers relative to the distal end.

In accordance with still another embodiment, a system is provided for localization of a region within a patient's body that includes one or more cameras for acquiring images of a body region of a patient's body to generate a model of the body region; and a probe. The probe may include a housing comprising a distal end configured for placement against a surface of the region towards one or more markers implanted within the body region; one or more antennas adjacent the distal end for transmitting electromagnetic signals into a patient's body and receiving reflected signals from the patient's body; a light source for delivering light pulses into a patient's body synchronized with the electromagnetic signals whereupon the markers modulate reflected signals from the respective markers; and a processor coupled to the one or more antennas configured to process modulated reflected signals from the one or more markers to determine distance values corresponding to distances from respective markers to the distal end; and determine coordinates of the one or more markers within the model of the body region.

Other aspects and features of the present disclosure will become apparent from consideration of the following description taken in conjunction with the accompanying drawings.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. For example, two components may be coupled to one another through an intermediate component. The phrases "attached to" or "attached directly to" refer to interaction between two or more entities that are in direct contact with each other and/or are separated from each other only by a fastener of any suitable variety (e.g., an adhesive).

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 2:
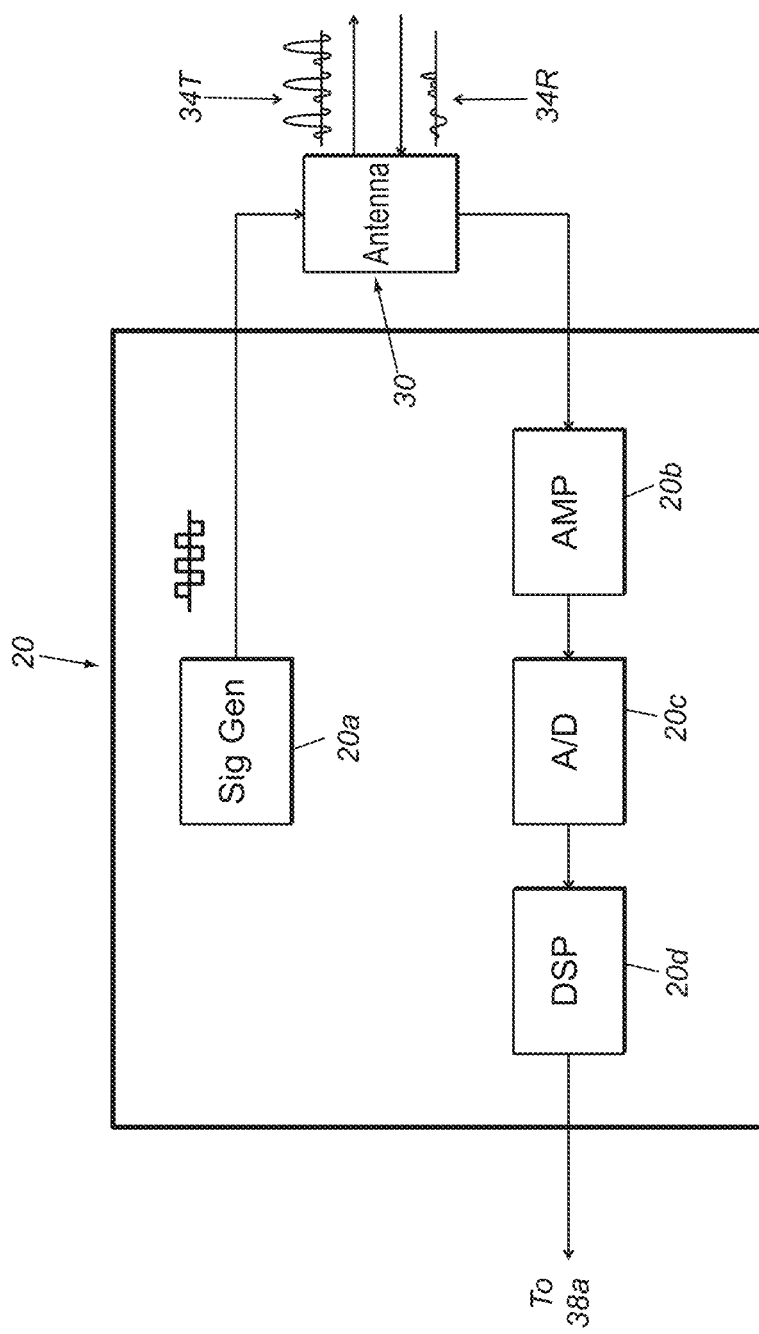
FIG. 2 is block diagram depicting exemplary components of the probe of FIG. 1.
Figure 3:
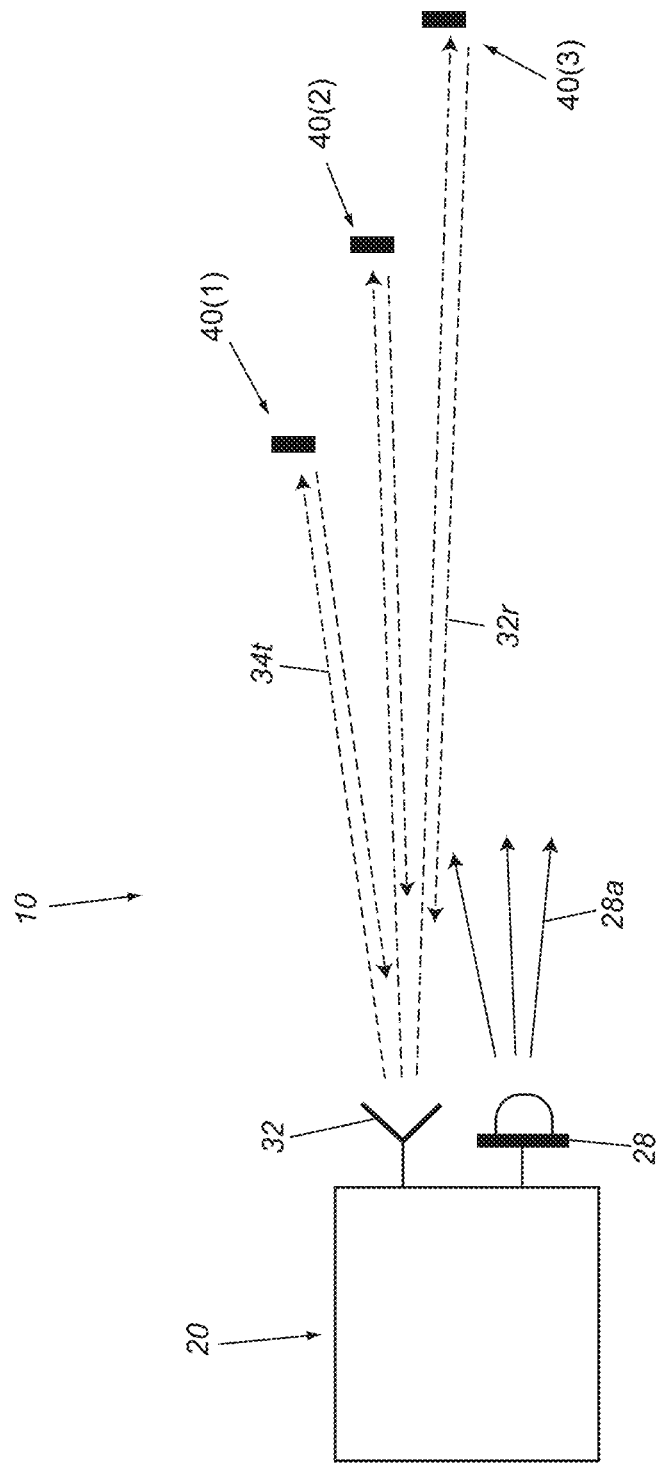
FIG. 3 is a schematic showing the system of FIG. 1 using the probe to identify and/or locate a plurality of markers that may be implanted within a patient's body.
Figure 10A:
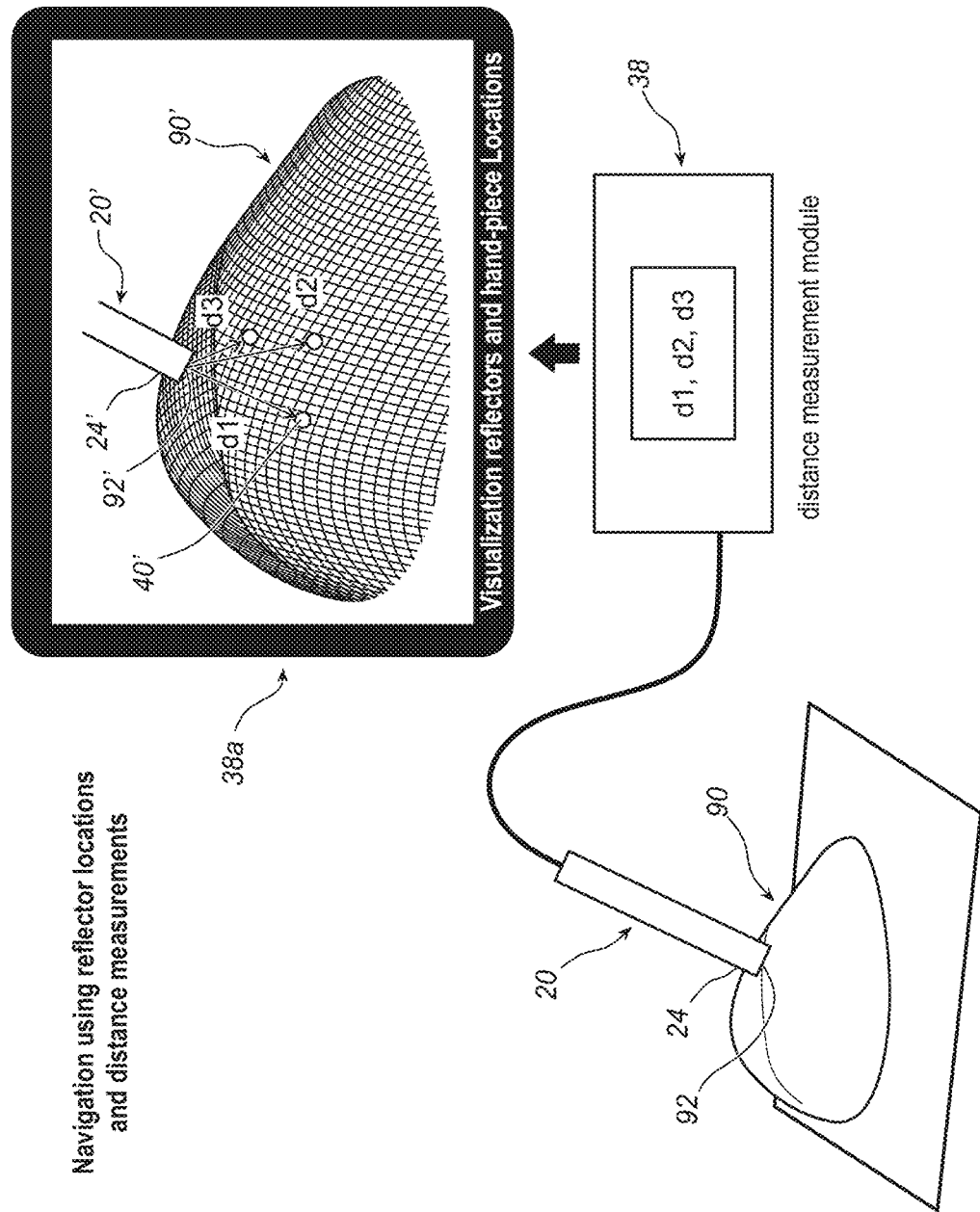
FIGS. 10A and 10B show a method for using localization of multiple markers implanted within a breast relative to the tip of the probe placed against the skin to identify the location of the tip at multiple locations on the breast to generate a three-dimensional model of the breast.
Figure 10B:
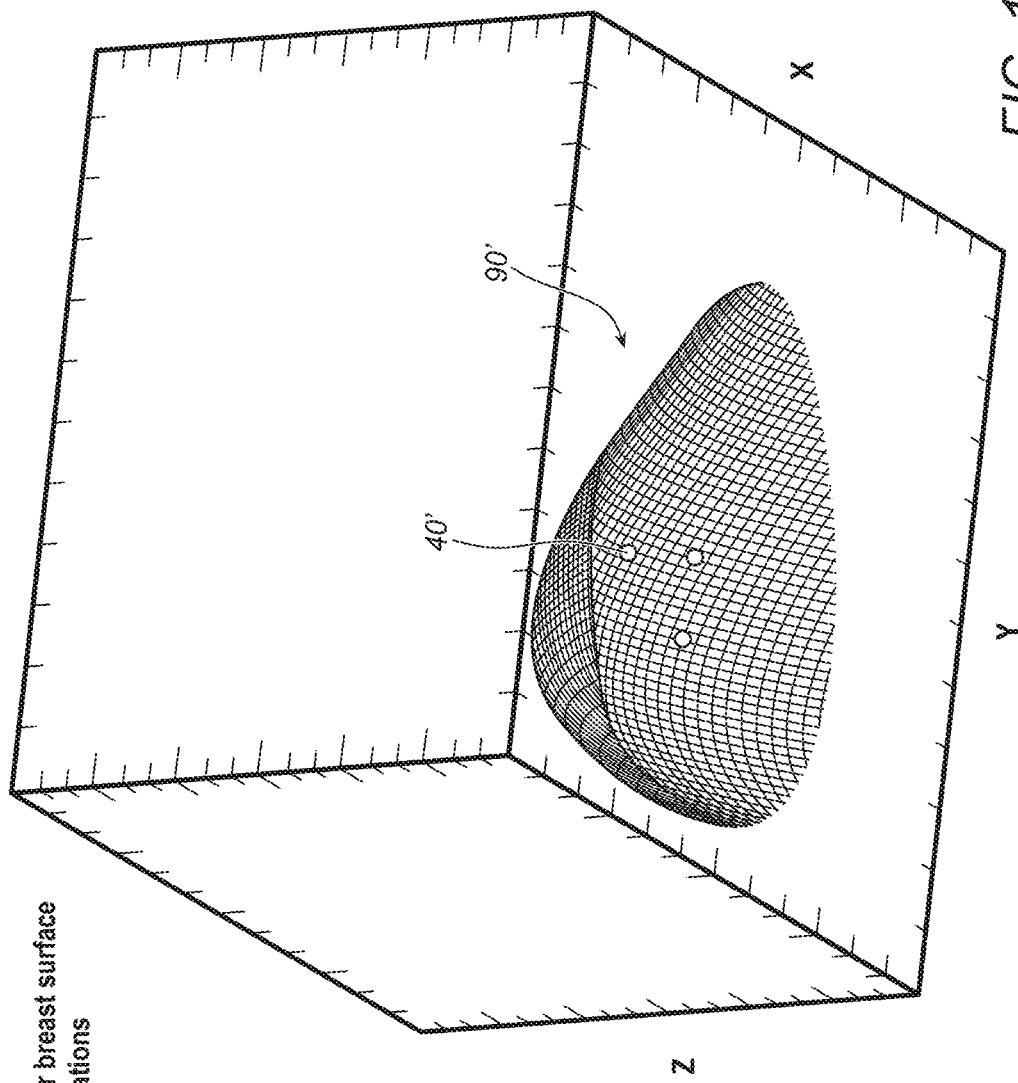

FIGS. 1-3 show an exemplary embodiment of a system 10 for localization of a target tissue region within a patient's body, e.g., for identifying and/or locating one or more markers 40 implanted within or adjacent a target tissue region, such as a tumor, lesion, or other tissue structure. In an exemplary embodiment, the system 10 may be used to generate a three-dimensional model of a body region of a patient, e.g., using a plurality of markers 40 as shown in FIG. 3, implanted with the body region to provide a reference frame, in anticipation of and/or during surgical or other medical procedures. For example, as shown in FIGS. 10A and 10B, a plurality of markers 40 may be implanted within a breast 90 for use during a biopsy or lumpectomy procedure, e.g., to generate a model to facilitate localization of a lesion or other target tissue region and/or to facilitate dissection and/or removal of a specimen from a breast 90, as described further elsewhere herein. It should be noted that, although the system 10 is described as being particularly useful in localization of breast lesions, the system 10 may also be used in localization of other objects in other regions of the body, e.g., as described in the applications incorporated by reference herein.

As shown in FIG. 1, the system 10 may include a delivery device 60 carrying one or more targets, tags, or markers (one marker 40 shown), a probe 20 for detecting and/or locating the marker 40 (or multiple markers 40(1)-40(N), e.g., the three markers shown in FIG. 3), and a controller and/or display unit 38 coupled to the probe 20, e.g., using one or more cables 36, generally similar to embodiments described in U.S. Publication Nos. 2011/0021888, 2014/0309522, 2016/0354177, 2017/0252124, 2017/0319102, and 2018/0279907, U.S. application Ser. No. 16/124,053, and U.S. provisional application Ser. No. 62/871,059, the entire disclosures of which are expressly incorporated by reference herein.

The probe 20 is a portable device having electromagnetic signal emitting and receiving capabilities. In some embodiments, the probe 20 is an elongate handheld device including a first or proximal end 22 which may be held by a user, and a second or distal end 24 intended to be placed against or adjacent tissue, e.g., a patient's skin or underlying tissue, defining a longitudinal axis 25 therebetween.

Figures 4A, 4B:
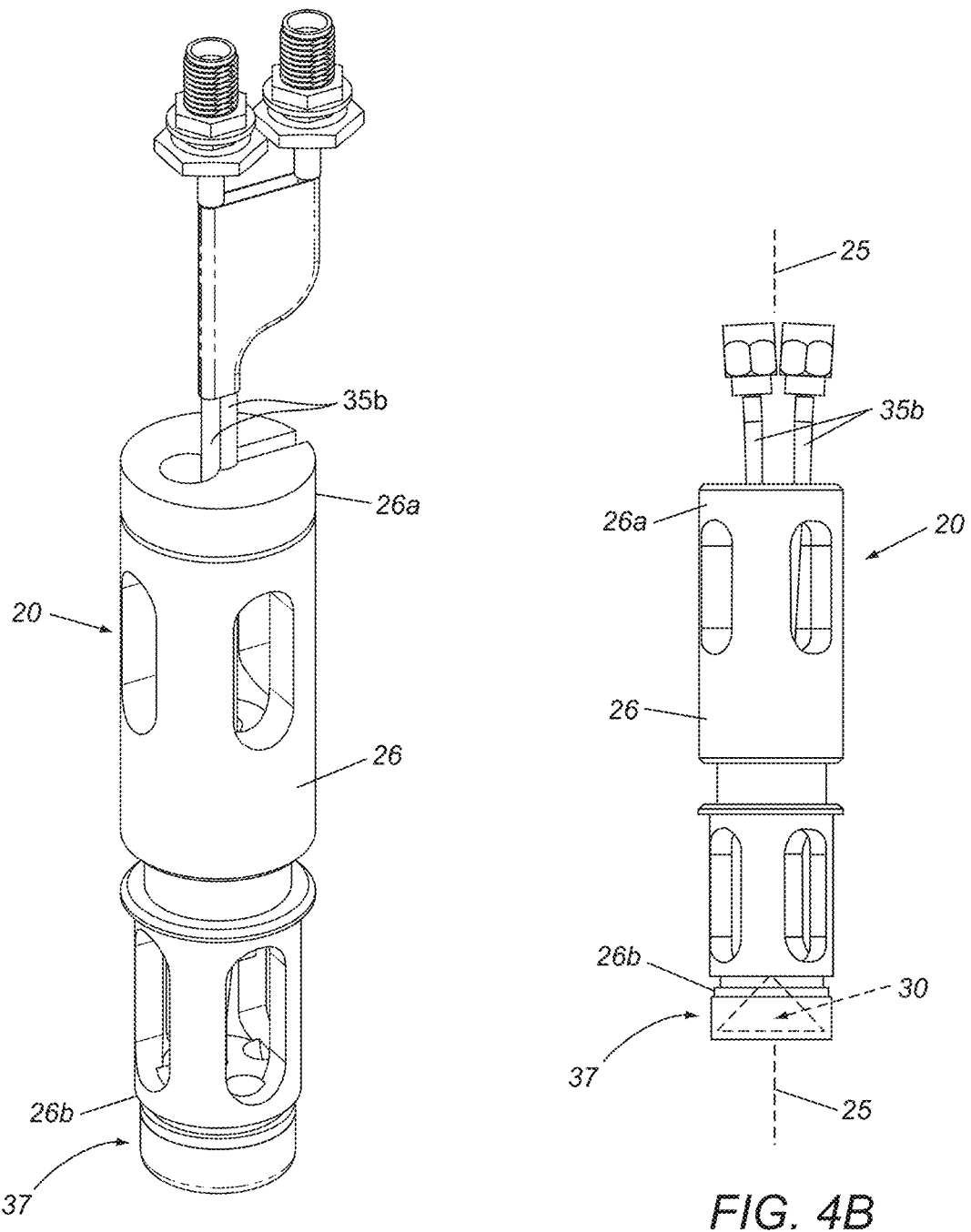
Figure 9:
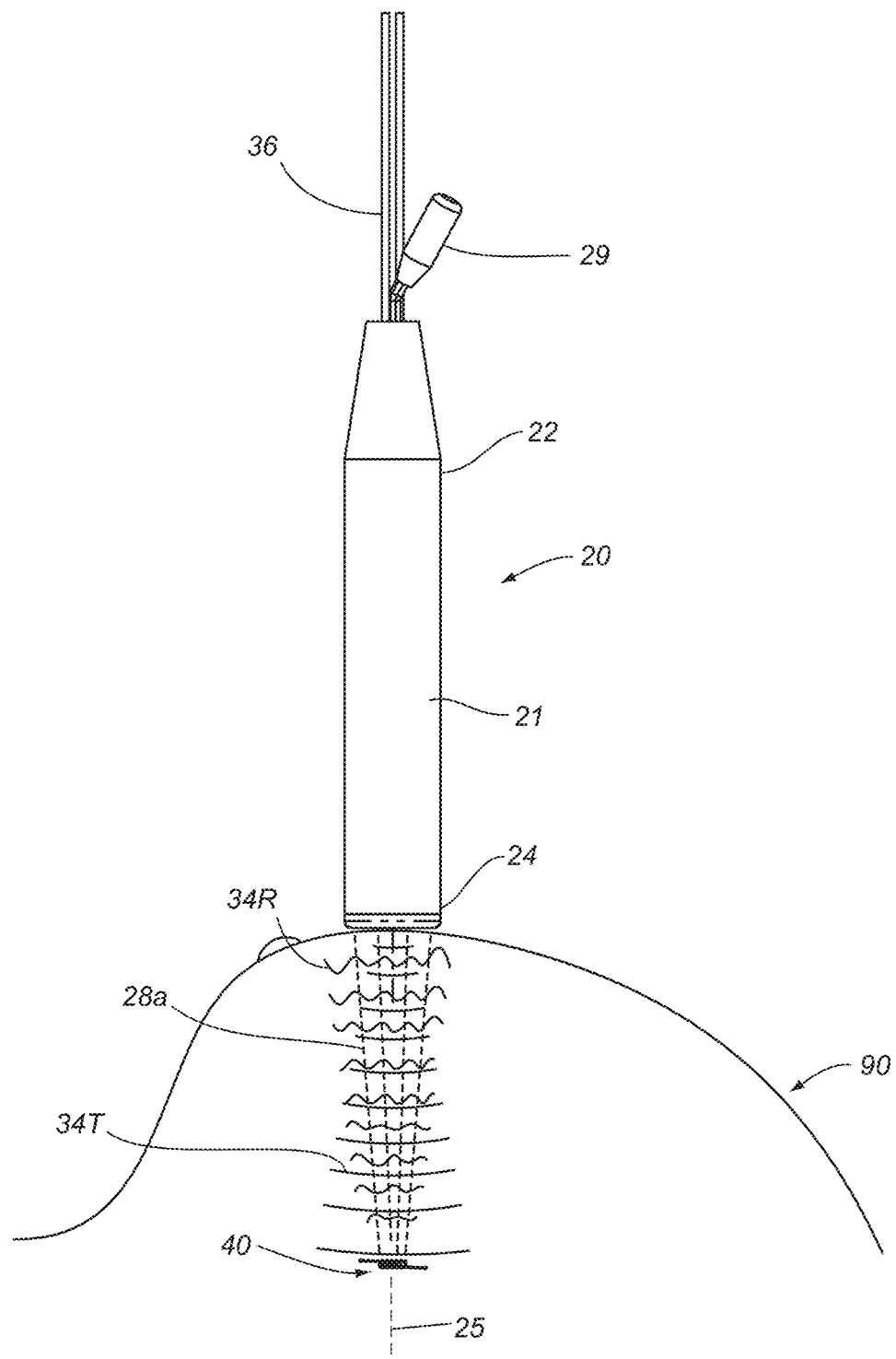
FIG. 9 is a side view of an exemplary embodiment of a probe localizing a plurality of markers implanted within a breast.

In some embodiments, the probe 20 includes one or more antennas 32, for receiving and transmitting mounted or carried on an antenna assembly 30. For example, as shown in FIGS. 4A-4C, including one or more transmit antennas 32T and receive antennas 32R on a base 32, as described further below. In addition, the probe 20 includes a light transmitter, e.g., a plurality of light fibers 28 (shown in FIG. 4C), configured to transmit light pulses 28a into tissue contacted by the distal end 24, e.g., generally along the longitudinal axis 25 into breast tissue 90, as shown in FIG. 9. The light fibers 28 may be coupled to a light source (not shown), e.g., by coupling 29 (shown in FIG. 9), such that light from the light source passes through the light fibers 28 distally from the distal end 24 of the probe 20.

In some embodiments, the probe includes one antenna for receiving and transmitting mounted or carried on the antenna assembly 30.

In an exemplary embodiment, the light source is an infrared light source, e.g., capable of delivering near infrared light between, for example, eight hundred and nine hundred fifty nanometers (800-950 nm) wavelength. Optionally, the light fibers 28 may include one or lenses, filters, and the like (not shown), if desired, for example, to focus the light transmitted by the probe 20 in a desired manner, e.g., in a relatively narrow beam extending substantially parallel to the longitudinal axis 25, in a wider angle beam, and the like. In another option, multiple light sources and/or filters may be provided to allow the probe 20 to deliver light pulses in different narrow bands. Alternatively, one or more light sources, e.g., IR LEDs, may be provided on the distal end 24 instead of light fibers 28 to deliver the light pulses 28a.

The probe 20 may include a processor within the probe housing 21 and/or display unit 38 including one or more circuits, signal generators, gates, and the like (not shown) needed to generate signals for transmission by the transmit antenna(s) 32T and/or to process signals received from the receive antenna(s) 32R. The components of the processor may include discrete components, solid state devices, programmable devices, software components, and the like, as desired.

FIG. 2 is a block diagram showing exemplary components of a controller of the probe 20 (although, alternatively, some of the components may be located within the controller/display unit 38 of FIG. 1). In the example shown, the probe 20 may include a signal generator 20a, an amplifier 20b, an analog-to-digital (A/D) converter 20c, and a digital signal processor (DSP) 20d. The signal generator 20a, e.g., a reference oscillator, produces an oscillating signal, such as a square wave signal, a triangular wave signal, or a sinusoidal signal.

For example, the probe 20 may include an impulse generator, e.g., a pulse generator and/or pseudo noise generator (not shown), coupled to the transmit antenna to generate transmit signals, and an impulse receiver for receiving signals detected by the receive antenna. The probe 20 may include a micro-controller and a range gate control that alternately activate the impulse generator and impulse receiver to transmit electromagnetic pulses, waves, or other signals via the transmit antenna, and then receive any reflected electromagnetic signals via the receive antenna, e.g., similar to other embodiments herein. Exemplary signals that may be used include microwave, radio waves, such as micro-impulse radar signals, e.g., in the ultralwide bandwidth region.

In the example shown in FIG. 2, a square wave signal may be sent from the signal generator 20a to the transmit antenna(s) 32T of the antenna assembly 30 of the probe 20. The antenna assembly may include a transmit antenna and a receive antenna. In some embodiments, the antenna elements may include a bowtie transmit antenna and a bowtie receive antenna with the transmit antenna offset ninety degrees (90°) from the receive antenna to define a Maltese cross antenna.

When the square wave signal passes through the transmit antenna(s) 32T, the transmit antenna(s) 32T may act as a band pass filter ("BPF") and convert the square wave signal to a series of pulses or other transmit signals 34T. As such, the transmit signals 34T (shown in FIG. 3) transmitted by the probe 20 may include a series of pulses. Alternatively, the probe 20 may be configured to transmit continuous wave signals, e.g., similar to embodiments described in the references incorporated by reference herein.

The transmit signals 34T may be transmitted into the tissue and reflected from the implanted marker(s) 40, as represented by the receive signals 34R shown in FIG. 3. Once the transmit signals 34T are reflected from the marker (s) 40, the reflected signals (i.e., the receive signals 34R) include a series of attenuated pulses (shown in FIG. 2).

As shown in FIGS. 2 and 3, the receive antenna(s) 32R of the antenna assembly 30 of the probe 20 may receive the receive signals 34R, which may be inputted into amplifier 20b in order to amplify the gain of the pulses. The output of the amplifier 20b may be inputted into an A/D converter 20c in order to convert the amplified analog signal into a digital signal. The digital signals output from the A/D converter 20c may be inputted into a DSP 20d for further processing. The DSP 20d may perform a number of processing functions including, but not limited to, calculating a difference in time from the time the transmit signals 34T were sent to the time the receive signals 34R were received (propagation time delay), determining the distance from the distal end 24 of the probe 20 to the marker 40, determining the location of the marker 40 relative to the distal end 24 of the probe 20, measuring the amplitude of the receive signals 34R, and/or determining the direction the marker 40 relative to the distal end 24 of the probe 20, e.g., as described in the references incorporated by reference herein.

Figure 11:
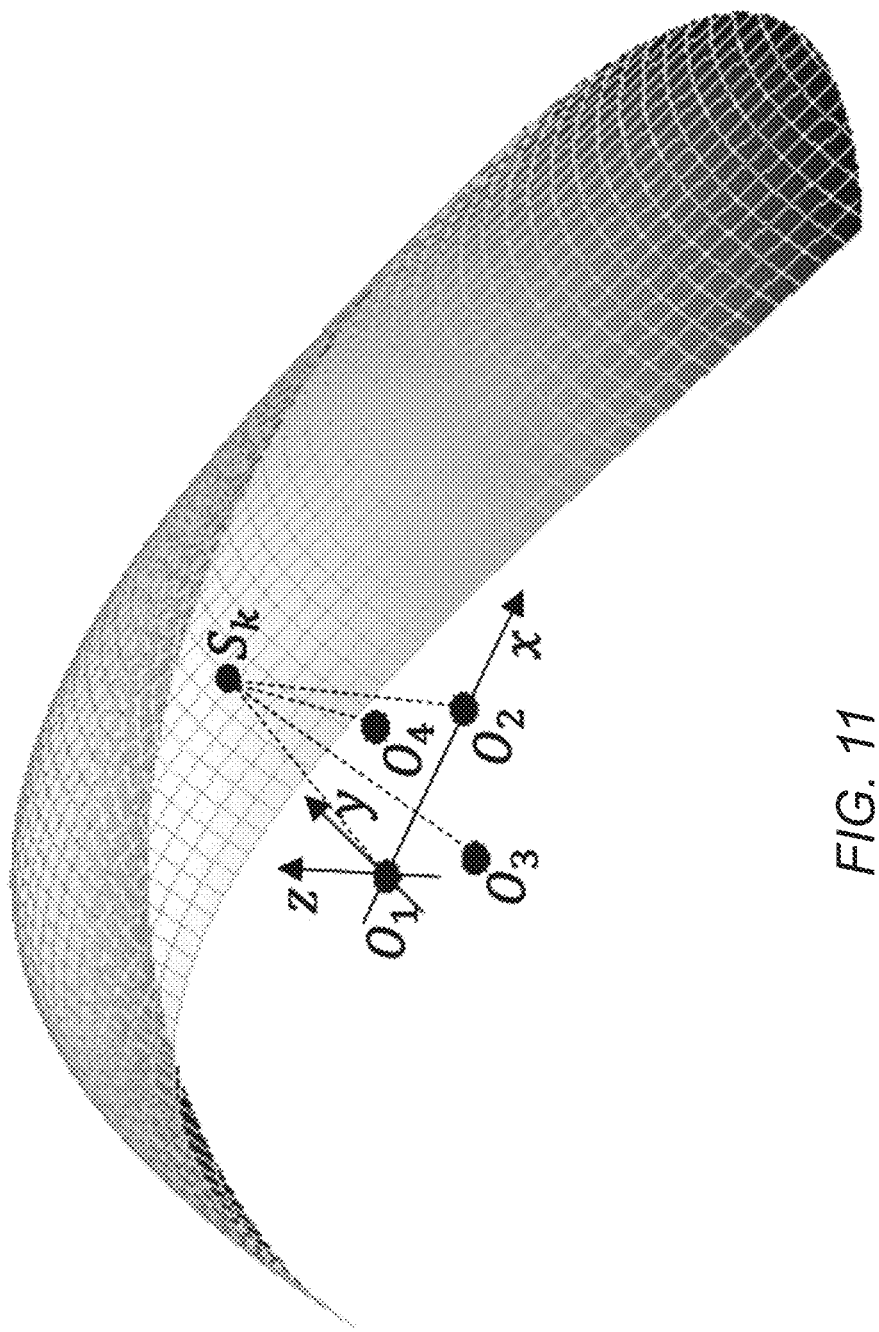
FIG. 11 is a schematic showing an exemplary algorithm for generating a coordinate system using a plurality of markers implanted within a body region.

The probe 20 may be coupled to a display 38a of the display unit 38, e.g., by cables 36, for displaying information to a user of the probe 20, e.g., spatial or image data obtained via the antennas 32R and/or other output from the DSP 20d. For example, FIG. 10B shows an exemplary output that may be presented, including a three-dimensional model of the markers within the body region, as described further elsewhere herein. As another example, FIGS. 10-11C show exemplary outputs that may be presented.

Optionally, the probe 20 may include other features or components, such as one or more user interfaces, memory, transmitters, receivers, connectors, cables, power sources, and the like (not shown). For example, the probe 20 may include one or more batteries or other internal power sources for operating the components of the probe 20. Alternatively, the probe 20 may include a cable, such as one of the cables 36, that may be coupled to an external power source, e.g., standard AC power, for operating the components of the probe 20.

As shown in FIGS. 1 and 9, the internal components of the probe 20 may be provided in an outer housing or casing 21 such that the probe 20 is self-contained, e.g., containing the components shown in FIGS. 4A-4D. For example, the casing 21 may be relatively small and portable, e.g., such that the entire probe 20 may be held in a user's hand. Optionally, a portion of the probe 20 may be disposable, e.g., a portion adjacent the distal end 24, or a disposable cover, sleeve, and the like (not shown) may be provided if desired, such that at least a proximal portion of the probe 20 may be reusable. Alternatively, the entire probe 20 may be a disposable, single-use device while the display unit 38 may be used during multiple procedures by connecting a new probe 20 to the display unit 38, which may remain out of the surgical field yet remain accessible and/or visible, as desired. Additional information on construction and/or operation of the probe 20 may be found in the references incorporated by reference elsewhere herein.

Turning to FIGS. 4A-4D, exemplary internal components of the probe 20 are shown (after removing the outer housing 21), e.g., including an internal sleeve or housing 26 carrying the antenna assembly 30, and, optionally, shielding 37, on or within its distal end 26b. With particular reference to FIG. 4D, the antenna assembly 30 includes a base 32 including a substantially planar distal surface 32a, e.g., extending perpendicular to longitudinal axis 25, and a plurality of proximal planar surfaces 32b including antenna elements 32T, 32R. Alternatively, a single proximal planar surface (not shown) may be provided opposite the distal surface 32a including antenna elements, similar to the probe 120 shown in FIGS. 13A-15 and described elsewhere herein, or in the embodiments in the references incorporated by reference herein.

The distal surface 32a may be located at a distal-most location of the distal end 24 of the probe 20, e.g., such that the distal surface 32a may be placed directly against a body surface, e.g., a patient's skin, tissue surface, and the like (e.g., covered with a thin membrane or cover to prevent fluids from entering the probe and/or other contamination).

The base 32 may be formed from ceramic and/or other nonconductive material, e.g., having desired dielectric properties. For example, the base 32 may be formed from material having a dielectric constant (permittivity) similar to the tissue type the probe is intended to be used with, e.g., a dielectric constant similar to human breast tissue, skin, muscle, bone, fat or other tissue.

In the configuration shown in FIG. 4D, the antenna elements may include a pair of transmit antennas 32T and a pair receive antennas 32R arranged in bowtie configurations on the proximal surfaces 32b of the base 32, e.g., with the transmit antennas 32T offset ninety degrees (90°) from the receive antennas 32R to define a Maltese cross antenna. Each of the antenna elements 32T, 32R may be formed separately and then attached to the corresponding proximal surfaces 32b or may be deposited directly onto the proximal surfaces 32b. In an exemplary embodiment, the antenna elements 32T, 32R may be formed from silver film or other material deposited onto the proximal surfaces 32b of the base 32.

Circuitry 35, e.g., a printed circuit board, flex circuit, and the like, may be coupled to the antennas 32T, 32R, e.g., including a PCB on which are provided one or more transformers and/or connectors (not shown) coupled to the respective antenna elements 32T, 32R by appropriate leads 35a. As shown in FIGS. 4A and 4B, coaxial cables or other leads 35b may be coupled to connectors on the PCB to allow the antenna elements 32T, 32R to be coupled to other components of the system, e.g., to cause the antenna elements 32T to transmit signals and/or to communicate received signals to other components of the system 10, similar to other embodiments described herein.

As shown in FIGS. 4C and 4D, the base 32 also includes a plurality of radial slots 33, e.g., a slot 33 between adjacent planar surfaces 32b. The slots 33 may extend axially from the distal surface 32a to the proximal surfaces 32b to substantially isolate the antenna elements 32T, 32R from one another by air within the slots 33, which may increase sensitivity, reduce crosstalk and/or other noise, and the like. Alternatively, the slots 33 may be filled with other insulating material, e.g., foam and the like (not shown), which may have a desired relatively low dielectric constant to substantially isolate the antenna elements 32T, 32R from one another. In addition, as shown in FIG. 4C, one or more light fibers or other light sources 28 may be positioned within one or more of the slots 33, e.g., to deliver light pulses beyond the distal surface 32a of the base 32, as described elsewhere herein.

Optionally, as shown in FIGS. 4A and 4B, the base 32 may be mounted within shielding 37, which may in turn, be coupled to the distal end 26b of the inner housing 26 (and/or the distal end 24 of the outer housing 21), e.g., by one or more of bonding with adhesive, sonic welding, fusing, cooperating connectors (not shown), and the like, similar to embodiments in the references incorporated by reference herein. The shielding 37 may have a length (i.e., along the axis 25) substantially longer than a thickness of the base 32 (i.e., the distance along the axis 25 from the distal surface 32a to a proximal end of the base 32). The distal surface 32a of the base 32 may be substantially flush with the distal end of the shielding 37 such that the distal surface 32a may contact tissue during use, as described elsewhere herein. Optionally, a Mylar film or other relatively thin layer of material (not shown) may be provided over the distal surface 32a of the base 32 and/or the shielding 37, e.g., to prevent fluids or other material entering the tip, reduce contamination, and/or otherwise protect the tip of the probe 20.

With continued reference to FIGS. 4A-4D, the proximal surfaces 32b of the base 32 may be exposed to a region of air within the shielding 37. Because of the low dielectric constant of air (e.g., close to one (1)), the air provides a dielectric or impedance mismatch with the material of the base such the transmission from the transmit antenna 32T is focused distally, i.e., towards the tissue contacted by the base 32. With the material of the base 32 chosen to substantially match the dielectric constant of tissue, the depth of transmission into the tissue may be enhanced. The air behind the base 32 may minimize lost energy that would otherwise be emitted by the transmit antenna 32T away from the tissue. The air behind the base 32 within the shielding 37 may also minimize crosstalk, noise and/or may otherwise enhance operation of the probe 20.

Turning to FIGS. 5A and 5B, an exemplary embodiment of a passive marker or tag 40 is shown that may be implanted within a patient's body, such as within a breast 90, e.g., as shown in FIG. 9. Generally, the marker 40 includes an electronics package 42 coupled to a pair of wires or antennas 44. In an exemplary embodiment, each wire 44 may be an elongate member, e.g., a solid or hollow structure having a diameter or other maximum cross-section between about half and two millimeters (0.5-2 mm) and a length between about one and ten millimeters (1.0-10 mm). The wires 44 may be formed from elastic or superelastic material and/or from shape memory material, e.g., stainless steel, Nitinol, and the like, such that the wires 44 are biased to a predetermined shape when deployed within tissue, but may be elastically deformed, e.g., to facilitate delivery, as explained elsewhere herein. Alternatively, the wires 44 may be substantially rigid such that the marker 40 remains in a substantially fixed, e.g., linear or curved, shape. As described elsewhere herein, the wires 44 may act as antennas and/or otherwise cooperate with electrical components within the electronics package 42.

As shown in FIGS. 5A and 5B, the wires 44 may be biased to assume a substantially linear configuration, e.g., such that the wires 44 extend substantially parallel to a longitudinal axis 48 of the marker 40. Optionally, one or both wires 44 may be offset from the longitudinal axis 48, which may enhance loading the marker 40 within a delivery device (not shown), as described elsewhere herein. Optionally, the wires 44 may carry one or more beads or other elements (not shown), e.g., similar to embodiments described in the references incorporated by reference herein.

As shown, each wire 44 may include a first end 44a coupled to a printed circuit board (PCB) or other circuit 50 within the package 42 and a second free end 44b terminating in an enlarged and/or rounded tip 45. Optionally, the first ends 44a may include one or more bends, e.g., to facilitate coupling the first ends 44a to the circuit 50 and/or such that the wires 44 extend tangentially from opposite sides of the package 42. Alternatively, the wires 44 may be biased to assume a curvilinear or other configuration, e.g., a helical, serpentine or other curved shape, around the longitudinal axis 48. For example, the wires 44 may be formed from elastic or superelastic material that is shape set such that the wires 44 are biased to the helical configuration shown, yet may be resiliently straightened to a substantially linear configuration, e.g., to facilitate loading the marker 40 into a delivery device and/or otherwise introducing the marker 40 into a patient's body, e.g., as described in the applications incorporated by reference herein.

With additional reference to FIG. 6, the marker 40 may include one or more circuits or other electrical components 50 encased or embedded in the electronics package 42 and configured to modulate incident signals from the probe 20. In an exemplary embodiment, a semiconductor chip, print circuit board (PCB), and/or other circuit 50 may be carried in the package 42 that includes a voltage or power source or other power or energy converter 52, a switch 54 that may be opened and closed when the energy converter 52 generate electrical energy, and an Electro Static Discharge (ESD) protection device 58.

In an exemplary embodiment, the energy converter 52 includes a plurality of photosensitive diodes capable of transforming incident light (e.g., infrared light) striking them into electrical energy (e.g., a predetermined minimum voltage). As shown, multiple pairs of diodes 52 may be connected in series, which may be arranged orthogonally to one another spatially within the package 42. The package 42 may be at least partially transparent or the diodes 52 may be exposed such that light directed towards the package 42 may be received by the diodes 52.

In the embodiment shown in FIG. 6, the switch 54 may be a field effect transistor (FET), e.g., a junction field effect transistor (JFET), with one end of the diodes 52 coupled to the gate (G) and the other coupled to the source (S), with a resistor 56 coupled between the gate (G) and the source (S), e.g., to discharge the diodes 52 when there is no IR light. In an exemplary embodiment, the switch 54 may include an enhancement mode pseudomorphic high electron mobility transistor (E-pHEMT), such as a VMMK-1225 manufactured by Avago Technologies US Inc., and the resistor 56 may be a three mega-Ohm (3 MΩ) resistor. In an alternative embodiment, the switch 54 may be a Schottky diode coupled to the diodes 52 (or other voltage source), e.g., with opposite ends of the diode coupled to the wires 44.

Also as shown, the source (S) of the switch 54 may be electrically coupled to one of the wires 44 and the drain (D) may be coupled to the other wire 44, e.g., such that the wires 44 provide an antenna for the marker 40. For example, the components of the circuit 50 may be mounted within the package 52 such that the components are electrically isolated from one another other than as coupled in the schematic of FIG. 6. The wires 44 may be bonded or otherwise attached to the package 52 such that ends of the wires 44 are electrically coupled to the switch 54 as shown.

Each diode 52 may be capable of generating sufficient voltage (e.g., about a half Volt (0.5 V)) when exposed to light to open and close the switch 54 when there is little or no load (i.e., current draw). Since the circuit 50 is intended to be merely modulate signals from the probe 1020, little or no current is needed, and so the power required from the diodes 52 (and consequently from the probe 1020) may be minimal, thereby reducing power demands of the marker 40 and probe 1020.

With additional reference to FIGS. 7A and 7B, light intermittently striking the diodes 52 may generate a voltage across the gate (G) and source (S) to provide a control signal that may open and close the switch 54. For example, FIG. 7A shows the switch 54 in the open configuration when infrared light is absent, while FIG. 7B shows the switch 54 in the closed configuration when infrared light 70 strikes the diodes 52, thereby connecting both wires 44 together. Thus, the result is that the marker 40 provides a passive tag that includes what equates to a high-frequency switch in the middle of the marker 40. By being able to change the switch 54 from closed to open, the reflection properties of the antenna provided by the wires 44 may be changed significantly.

Specifically, the marker 40 is made to periodically change its structure between two form factors, e.g., the reflectors shown in FIGS. 7A and 7B. For example, as described further elsewhere herein, digital signal processing of the received signals using ultra-wideband (UWB) radar uses synchronous detection of the signal modulated with marker switching frequency. This significantly increases the signal-to-noise (SNR) on the marker signal because other contaminating signals remain unchanged within the modulation period. To provide a mechanism for a synchronous detector, the marker switching process is controlled in the probe 20 by illuminating breast tissue with near infrared (IR) light pulses that are received by the marker 40.

Switching of the marker reflective form-factor is controlled with the set of diodes 52 operating in photovoltaic mode. When the diodes 52 receive light from the probe 102 (represented by arrows 70 in FIG. 7B), the diodes 52 generate voltage that is applied between the gate (G) and source (S) of the switch 54, which closes and connects together the drain (D) and source (S) making both antenna wires 44 connected together, as shown in FIG. 7B. When the light is off, the switch 54 is open and the drain (D) and source (S) are electrically disconnected, as shown in FIG. 7A.

In addition, the markers may include one or more features to facilitate identifying and/or distinguishing individual markers when multiple markers are implanted within a body region, e.g., to allow the probe 20 to simultaneously or sequentially identify and localize each of the markers. For example, in one embodiment, a plurality of markers may be provided, with each marker including a clock circuit or block (not shown) coupled to the diodes 52 and a sequence generator (also not shown) coupled to the clock circuit and the switch 54 to generate a code sequence to open and close the switch 54 to modulate signals reflected by the marker 40 back to the probe 20 based on the code sequence. The sequence generator of each marker 40 may be pre-programmed such that the code sequences generated by the sequence generators are orthogonal to one another, i.e., the sequence generators may open and close the respective switches 54, based on the light pulses from the light source 28 of the probe 20, to modulate the reflective properties of the markers 40 differently from one another. The probe 20 may be configured to analyze the reflected signals to identify and locate each of the markers 40 substantially simultaneously based on the resulting modulation in the reflected signals received by the probe 20, e.g., as described in U.S. application Ser. No. 16/124,053 incorporated by reference herein.

In addition or alternatively, the package 42 and/or the diodes 52 may include one or more coatings and/or filters, e.g., to allow the probe 20 to communicate individually, e.g., sequentially, within individual markers, similar to markers disclosed in U.S. Publication Nos. 2017/0252124 and 2017/0319102, incorporated by reference herein. For example, the probe 20 may be capable of delivering separate narrow bands of infrared light and the markers may include filters (not shown) such that individual markers may only receive respective narrow bands, thereby allowing the probe 20 to modulate and identify, individual markers. Alternatively, the markers may include processors (not shown) that analyze light pulses from the probe 20 such that the processors may identify commands from the probe 20, e.g., to modulate individual markers. In this manner, the probe 20 may be able to activate and/or modulate individual markers such that the probe 20 may identify and/or locate the markers sequentially by sending commands in the light pulses to activate individual markers in a desired sequence, e.g., as described in the references incorporated by reference herein.

Optionally, in embodiments where individual markers 40 are localized sequentially, the system may provide one or more outputs to identify which marker is currently being localized. For example, in the display 38*a* shown in FIG. 1, the bar or other output of an active marker may be distinguished from the other dormant markers, e.g., by changing a color of the output, e.g., distance bar or identifier, and the like. In addition or alternatively, a speaker may generate a different output, e.g., a different pitch, tone, or other sound, to identify the active marker and/or otherwise distinguish it from dormant markers during sequential localization.

Returning to FIGS. 1-3 and with additional reference to FIGS. 9, 10A, and 10B, the system 10, e.g., including the probe 20 and implanted markers 40, may be used to generate a three-dimensional model 90' of a body region of a patient, e.g., breast 90, based on absolute or relative locations of the markers 40, e.g., in anticipation of and/or during a surgical or other medical procedure. As shown in FIGS. 10A and 10B, the model 90' may be presented on a display 38*a*, e.g., to facilitate localization of a lesion or other target tissue region within a breast 90 and/or to facilitate dissection and/or removal of a specimen from the breast 90, e.g., before and/or during a lumpectomy procedure.

Figure 8A:
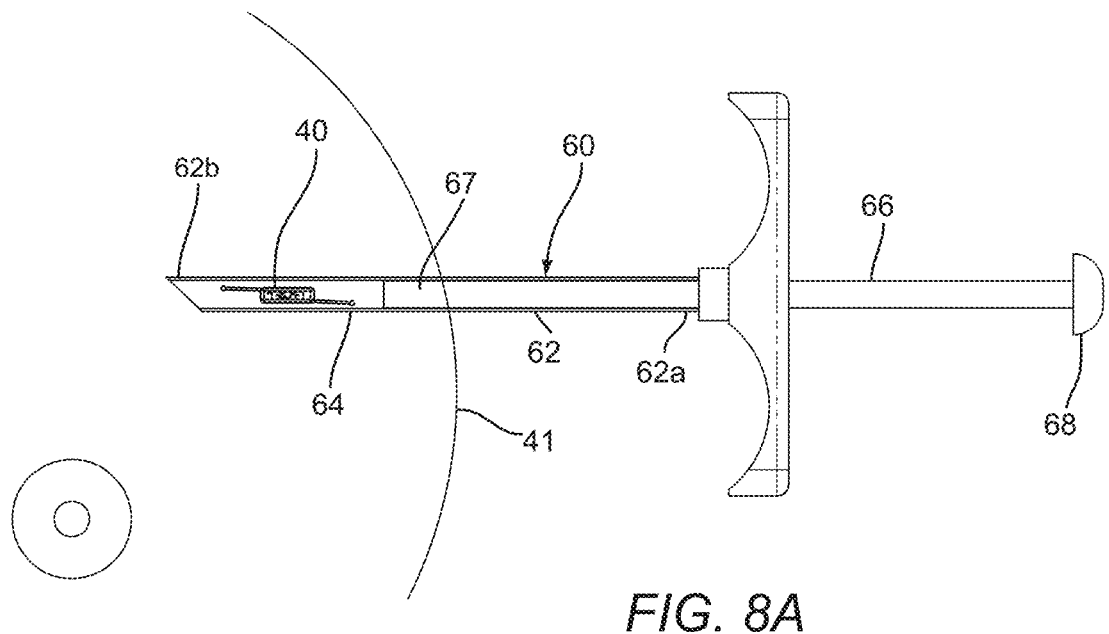
FIGS. 8A and 8B are side views of a breast, showing a delivery device being used to deliver a marker into tissue within the breast.
Figure 8B:
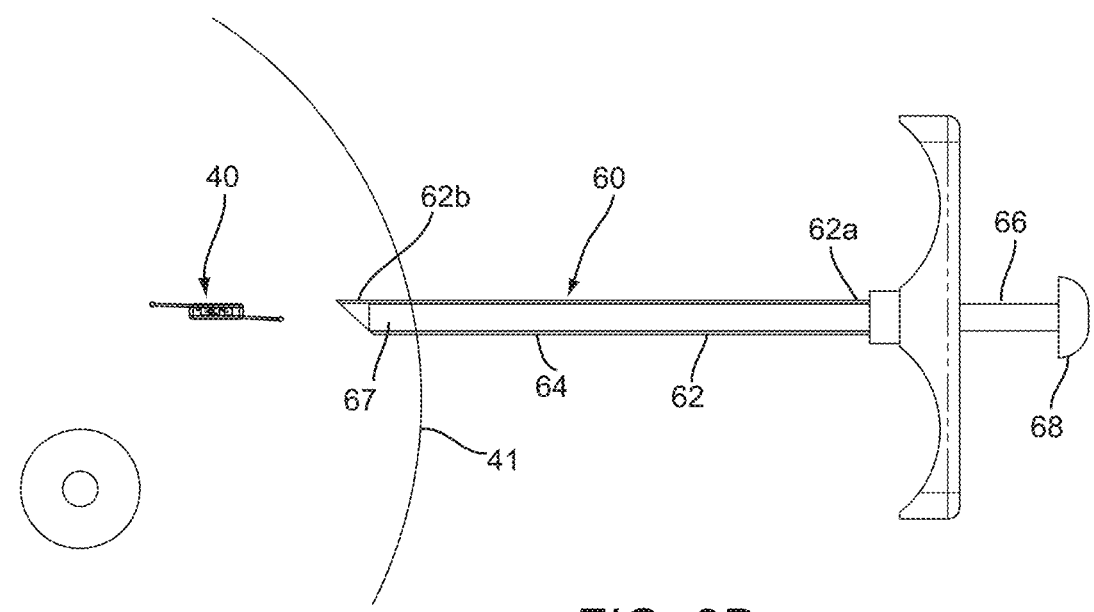

FIGS. 8A and 8B illustrate a delivery device 60 being used to deliver a marker 40 into tissue within the breast tissue 90. As shown, the delivery device 60 may include a lumen 62 and a plunger 68. The plunger 68 may include a piston that extends into the lumen 62 and is slidable within the lumen 62. To introduce the marker 40 or markers within the breast tissue 90, the marker may be positioned in the lumen 62 and the lumen may be inserted into the tissue. The plunger 68 may be advanced to cause the piston to push the marker(s) 40 from the lumen 62.

Before a procedure, a target tissue region, e.g., a tumor or other lesion, may be identified using conventional methods. For example, a lesion (not shown) within a breast 90 may be identified, e.g., using mammography and/or other imaging, and a decision may be made to remove the lesion. One or more (e.g., three) markers 40 may be implanted within the breast 90 within or adjacent the lesion, as shown in FIG. 9, e.g., using a needle or other delivery device, such as the delivery device 60 shown in FIGS. 8A and 8B, as described further in the references incorporated by reference herein.

For example, the markers 40 may be implanted within the breast 90 in a three dimensional array surrounding the lesion or otherwise spaced apart from one another and the lesion, e.g., to define a desired margin or volume, e.g., of a target specimen for removal around the lesion. Once the markers 40 are implanted, a model may be generated at any time after implanting the markers 40, e.g., immediately after implanting the markers 40 to facilitate planning a procedure. In addition or alternatively, the model may generated immediately before the procedure, e.g., within the surgical setting for use by the surgeon to monitor dissection and/or removal of a specimen during the procedure.

Generally, as shown in FIGS. 10A and 10B, the model 90' of the breast 90 may be presented on the display 38*a*, which may also include representations of the markers 40' and/or probe 20.' Presenting such a model 90' on a display 38*a* during the procedure may facilitate a surgeon identifying the location of the markers 40 within the breast 90 and thereby, identify the location of the lesion within the breast 90, e.g., relative to the distal end 24 of the probe 20, which may be used by the surgeon during the lumpectomy procedure to identify a path for dissection and/or removal of the specimen, e.g., including the lesion and markers 40.

In an exemplary method for generating the model 90' (once the markers 40 are implanted), as shown in FIGS. 9 and 10A, the distal end 24 of the probe 20 may be placed in contact with or adjacent the patient's skin, e.g., generally above the lesion, and/or otherwise aimed generally towards the lesion and markers 40, and activated to determine a spatial relationship between the markers 40 and the distal end 24 of the probe 20. The probe 20 may then be moved to one or more additional surface locations, e.g., to obtain a reference frame and/or generate the model 90'.

For example, initially, the distal end 24 of the probe 20 may be placed against the patient's skin (or other surface) at a first surface location 92, e.g., as shown in FIG. 10A, and the probe 20 may be activated. As described elsewhere herein, signals from the antenna(s) 32T of the probe 20 may be delivered along with pulsed light from the light source to cause the switches 54 to open and close as the markers 40 receive and reflect signals back to the probe 20. The reflected signals from the two states (switches 54 open and closed) may be subtracted from one another, substantially eliminated other noise, and allowing the probe 20 to identify and/or locate the markers 40. The probe 20 may acquire signals from the markers 40 substantially simultaneously, e.g., using orthogonal code sequences, or sequentially by activating and/or polling the markers 40 sequentially, as described elsewhere herein and in the references incorporated by reference herein.

The processor of the probe 20 may then identify and/or localize the markers 40 based at least in part on the reflected signals. For example, based on propagation time delay between the transmitted signals 34T and received reflected signals 34R, distances d1, d2, d3 may be determined from the markers 40 to the distal end 24, e.g., substantially simultaneously or sequentially, thereby providing distances from the markers 40 to the distal end 24 (and consequently to the first surface location 92 on the breast 90, as described further below). Optionally, the display 38*a* may present information to the user related to the location of the markers 40 relative to the probe 20 based on the current location of the distal end 24. For example, as shown in FIG. 1, the display 38*a* may include a readout on a portion thereof providing distances from each of the markers 40 to the distal end 24 of the probe 20. The distance information may be displayed as a numerical value representing the distance in units of length, such as in inches (in.) or centimeters (cm).

The probe 20 may then be moved to a second location (not shown), e.g., by sliding the distal end 24 along the patient's skin or lifting and moving the distal end 24 for a desired distance from the first location 92. The markers 40 may then again be identified and localized, e.g., to provide distance information from the markers 40 to the distal end 24 at the second location. Optionally, the probe 20 may be moved one or more additional times to acquire distance information from one or more additional locations.

Based on at least some of the distance information, the processor of the probe 20 may obtain a reference frame, e.g., a three-dimensional x-y-z or other orthogonal reference frame, based on the locations of the markers 40 within the breast 90. Thus, the reference frame may be fixed relative to the breast and its associated structures, e.g., the overlying skin.

Once the reference frame is established, the processor may generate the model 90,' e.g., by using trilateration, i.e., the distances d1-d3 from the markers 40 to the respective surface locations where the distances were acquired. For example, for the first location 92 shown in FIG. 10A, the processor may use the distances d1-d3 to determine an x-y-z coordinate location of the first location 92. The processor may then map this on the model to identify the first location as represented by location 92' in the display 38a of FIG. 10A since the distances d1-d3 may map to a unique location relative to the markers 40. This process may be repeated for each of the surface locations to identify multiple locations of the patient's skin. Once sufficient samples have been taken, the processor may predict the surface of the breast 90 and present the resulting model 90' on the display 38a, e.g., as shown in FIG. 10B. The number of samples to generate the model 90' may be based the size of the surface of the body region, e.g., breast 90, and/or the desired granularity of the model 90' to be displayed.

Once the model 90' has been constructed, the processor may identify the current location of the distal end 24 of the probe at any time and then add a representation of the probe 20' to the model 90', as shown in FIG. 10A. Using this presentation, the surgeon may be able to observe in real time the location of the distal 24 of the probe 20 relative to the markers 40, and therefore, relative to the lesion, simply by observing the model 90' and the corresponding representations for the distal end 24' and the markers 40." For example, based on this information, the surgeon may decide on the shortest and/or easiest path to the lesion, create an incision at a desired location in the patient's skin and dissect intervening tissue to a desired depth, e.g., corresponding to a target margin around the lesion is reached. At any time, the distal end 24 of the probe 20 may be inserted into the incision and/or otherwise placed against tissue to confirm the location of the markers 40 and lesion. Using this information, a tissue specimen may be excised or otherwise removed using conventional lumpectomy procedures, e.g., with the markers 40 defining the desired margin or volume, and/or remaining within the removed specimen. In addition, if for some reason a body region that has already been modeled has moved, e.g., if the patient moves or is reoriented, at any time, the surgeon or other user, may generate a new model simply by repeating the process using the probe to localized the markers within the region.

Turning to FIG. 11, an exemplary algorithm will now be described, which may be used to obtain a reference frame and/or generate a model by localizing a plurality of markers implanted within a tissue structure, e.g., by simultaneously measuring the propagation time delays between the radar antenna (i.e., the distal end 24 of the probe 20, not shown) and individual markers within a group of implanted markers. The markers may be distinguished using preprogrammed orthogonal modulation codes, enable the probe to evaluate the distances to the markers from multiple locations substantially simultaneously.

Calculations of the markers and probe locations from distance measurements may be performed using known methods of computational geometry and geometry algebra dealing with distance geometry problems. Various methods for solving distance geometry problems have been developed for visualization of graphs given by set of nodes and lengths of edges connecting them. Such types of problems frequently occur in presentation and analysis of network structures, in molecular physics, robotics and other fields (see, for example a review by L. Liberti et al "Euclidian Distance Geometry and Applications" *SIAM Review*, 2014, Vol. 56, No 1, pp. 3-69, the entire disclosure of which is expressly incorporated by reference herein). Many different methods developed for distance geometry problems may be applicable to the systems and method herein.

With continued reference to FIG. 1, consider multiples markers $O_l$, l=1 . . . N, placed in breast tissue to indicate the location of a tumor, for the case of four markers, i.e., case N=4. Radar placed on the surface of the breast at point $S_k$ can evaluate a set of distances $d_{kl}$=dist$\{S_k, O_l\}$, l=1 . . . N to each marker $O_l$ using simultaneous measurements of round-trip propagation times for each marker. To achieve the simultaneous measurements of the propagation times, each marker is configured to reflect radar signals with a preset code of reflected modulation, enabling radar to distinguish the marker echoes in the received signals by using one of the methods of code division multiplexing, for example, those disclosed in U.S. application Ser. No. 16/124,053, incorporated by reference herein. FIG. 11 illustrates the geometry (a graph) of a single measurement and a method for selection of the reference coordinate systems (x, y, z) linked with the markers. The coordinate system maybe defined using positions of specific markers, for example, where location of $O_1$ defines the origin of the coordinate system, line connecting $O_1$ and $O_2$ the x-axis. The reflectors $O_1$ and $O_2$ together with one of the remaining reflector, e.g. $O_3$, can define the (x, y) plane, i.e., z=0. Therefore, the coordinates of the preselected markers defining the reference coordinate system will be $O_1(0,0,0)$, $O_2(x_2, 0,0)$ and $O_3(x_3, y_3, 0)$. Assuming that each measurement provides N distance values $d_{kl}$=dist$\{S_k, O_l\}$, l=1 . . . N, for M measurements at different locations, $S_k$, k=1 . . . M one will have MN distances given by the following set of equations $$d_{kl} = \sqrt{(\bar{x}_k - x_l)^2 + (\bar{y}_k - y_l)^2 + (\bar{z}_k - z_l)^2}, \, k=1 \ldots M, \, l=1 \ldots N, \quad (1)$$

where variables marked with bar corresponds to (x, y, z)-coordinates of $S_k$ points. The number of equations in system (1) is given by the number of distance measurements and equals to MN, while the number of unknown variables equals to 3N+3M−6. Here the last term, −6, is due to the use of known coordinates for preselected reflectors $O_1$, $O_2$ and $O_3$ in 3D space. To find all unknown coordinates for reflectors $O_l$, l=2 . . . N and radar positions $S_k$, k=1 . . . M, the number of equations should be equal or greater than the number of unknowns. Therefore, the number of reflectors N and measurement sites M with simultaneous measurements of distances to all reflectors should satisfy the following condition $$3N+3M-6 \leq MN, \quad (2)$$

which can be rewritten as $$M \geq \frac{3(N-2)}{(N-3)}$$

Taking into account that setup of reference coordinate system in 3D space requires at least three reflectors (N≥3), the minimal number of reflectors suited in this method is N=4 and, therefore, the minimal number of required measurements is M=6.

Since the systems of distance equations (1) consists of quadratic equations with multiple sets of solutions, an additional analysis is needed to select the right solution set that satisfy the configuration of reflectors and measurement points. Use of additional constraints based on the expected configuration of reflectors and position of measuring points may be required for such selection.

From the viewpoint of graph theory, the considered structure of nodes, N and M, with the corresponding edges $d_{kl}$ computed as (1) form a bipartite graph in Euclidian space of dimension d=3. It is known that a graph containing n nodes will form a rigid framework in the space of dimension d if the number of edges equals or more than (see for example, B. Hendrickson, "Conditions for Unique Graph Realizations", *SIAM J. Comput.* 1992, Vol. 21, No. 1, pp. 65-84), the entire disclosure of which is expressly incorporated by reference herein).

$$nd-d(d+1)/2, \text{ if } n \geq d.$$

$$n(n-1)/2, \text{ otherwise.} \quad (3)$$

In the present case, n=N+M, d=3 and n≥d. Therefore, minimum number of edges (i.e., the minimum number of measured distances, $d_{kl}$) should be 3n−6=3N+3M−6 or, in the present case of bipartite graph, containing NM edges, this condition is equivalent to the condition (2) that guarantee the matching the number of unknowns to the distance equations (1).

A possible approach to the solution of position problem is to use one of the known point fitting approach to fine locations of all $O_l$ and $S_k$ points. For example, this can be done by minimization of errors in the fitting node locations ($O_l$ and $S_k$) for a given set of distances between them. Such an error can be defined as $$E = \Sigma_{k=1}^{M} \Sigma_{l=1}^{M} (d_{kl} - \sqrt{(\overline{x}_k - x_l)^2 + (\overline{y}_k - y_l)^2 + (\overline{z}_k - z_l)^2})^2$$

where $x_1$=0, $y_1$=0, $z_1$=0, $y_2$=0, $z_2$=0 and $z_3$=0 are fixed values. The value of E approaches zero when the all coordinates of the points ($O_l$ and $S_k$) form a graph that fits to all measured distances $d_{kl}$, for k=1 . . . M, l=1 . . . N. By construction, the E is a positively defined function that can be used as a cost function. Other types of cost functions known in the literature can be constructed for evaluation of total error. Various known methods of optimization can be used to find the minimum of such a cost function that will correspond to the solution for the nodes ($O_l$ and $S_k$) locations.

Another approach to solving this localization problem is to use methods of spring embedders and force directed graph-drawing algorithms. In this approach, edges are considered as springs of lengths $d_{kl}$ connecting the corresponding nodes and the cost function E represents the total potential energy of the spring system. Force between the nodes produced by the springs tends to place the nodes in the positions where distance between the nodes equal to the lengths of the unloaded springs and therefore the measured distances $d_{kl}$. Various algorithms for such computation of the graph realization is discussed in the literature, see, for example, S. G. Kobourov, Spring Embedders and Force Directed Graph Drawing Algorithms, arXiv:1201.3011v1 [cs.CG] 14 Jan. 2012, the entire disclosure of which is expressly incorporated by reference herein.

Figure 12A:
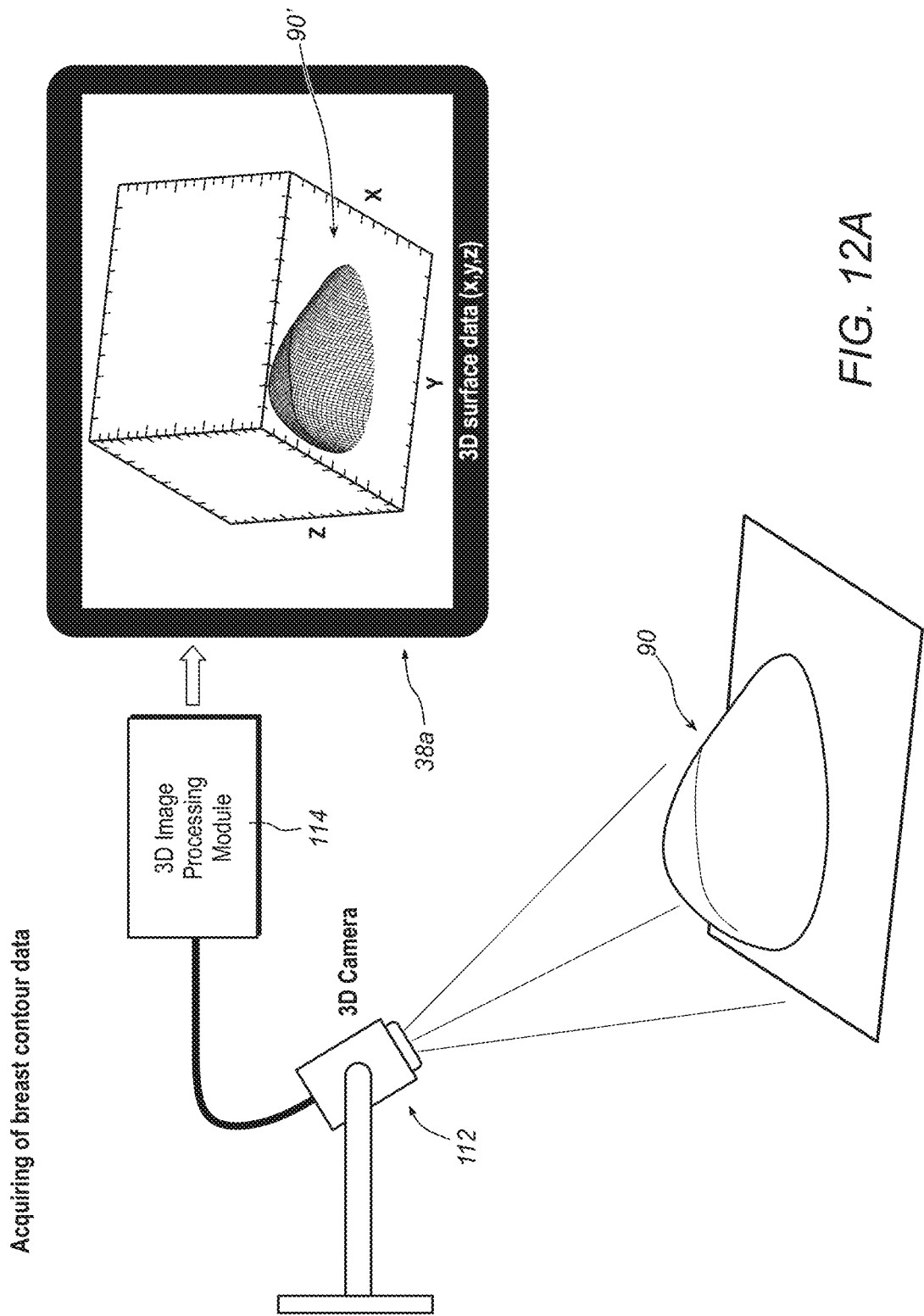
FIGS. 12A and 12B show a system and method for generating a three-dimensional model of a breast using an external camera in conjunction with a probe that localizes a marker within the breast.
Figure 12B:
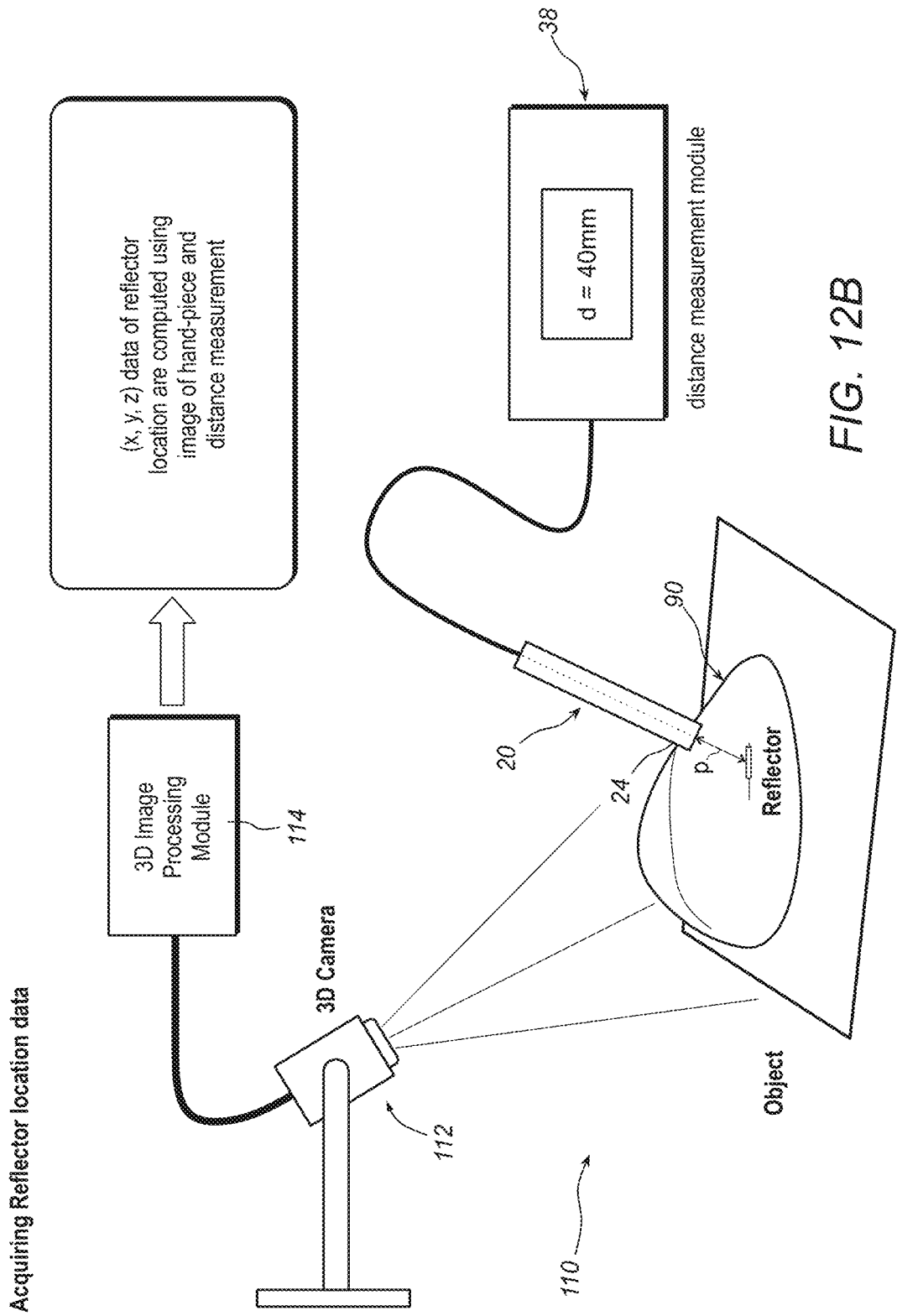
Figure 13A:
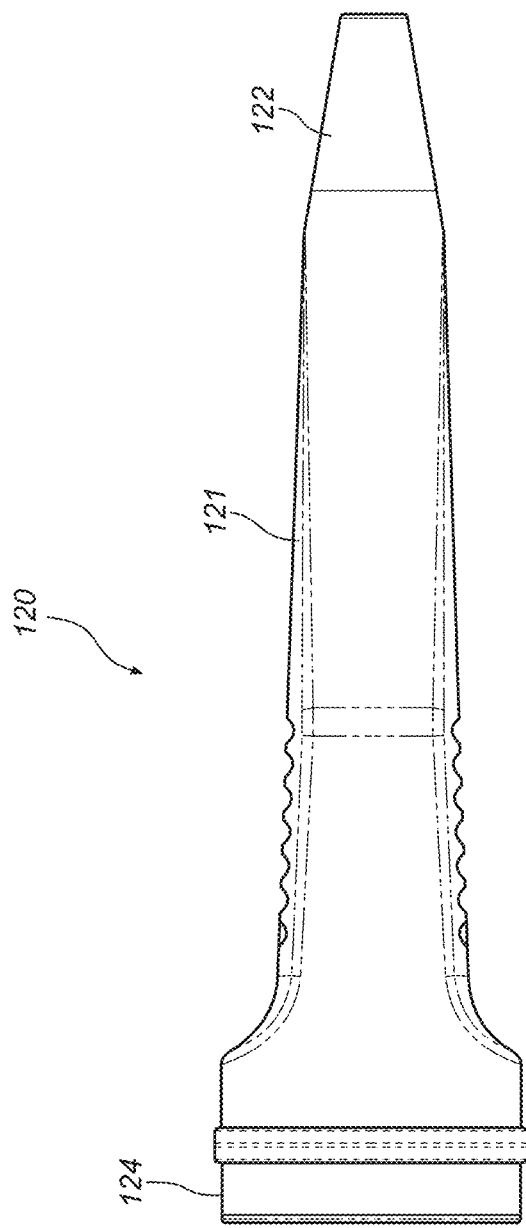
FIGS. 13A and 13B are side and end views of another exemplary embodiment of a probe including a single transmit antenna and a plurality of receive antennas to generate a three-dimensional model of a body region.
Figure 13B:
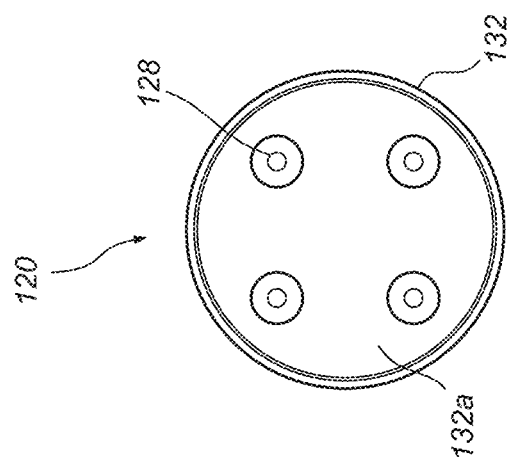

Turning to FIGS. 12A and 12B, another system 110 is shown for generating a model of a body region, such as a breast 90. Generally, similar to other embodiments herein, the system 110 includes a probe 20, e.g., including a processor and display 38a (along with other components similar to other probes 20 herein) and one or more markers 40 that may be implanted within the breast 90 (one marker 40 shown), e.g., to identify the location of a lesion. Unlike previous embodiments, the system 110 also includes one or more external cameras, e.g., 3D camera 112, which may be mounted or otherwise fixed relative to its surroundings, e.g., fixed relative to a bed on which a patient may lie and/or relative to an operating room or other setting within which the patient will be presented to generate the model. The camera 112 may be coupled to a 3D image processing module 114, which may be a separate device or may be included in the controller 20 coupled to the probe 20.

During use, the camera 112 may acquire one or more two-dimensional or three-dimensional images of the body region, e.g., breast 90, and the processing module 114 may process the image(s) to generate the three-dimensional model 90', which may be presented on display 38a and/or stored in memory of the processing module 114 or controller 38.

The probe 20 may then be used to localize the marker(s) 40 implanted within the breast 90, e.g., by placing the distal end 24 against the patient's skin and activating the probe 20. For example, electromagnetic signals, e.g., ultra-wide band radar signals, from the probe 20 may be delivered along with pulsed light to cause a switch (not shown) of the marker 40 to open and close to modulate reflected signals from the marker 40, allowing the probe 20 to identify and/or locate the marker 40, e.g., to determine a distance d from the marker 40 to the distal end 24, as shown in FIG. 12B.

Simultaneously, the camera 112 may acquire one or more images of the breast 90 and probe 20. The processing module 114 may process the image(s) to identify the location of the distal end 24 of the probe relative to the breast 90, e.g., to identify the surface location on the patient's skin where the distal end 24 is contacting the breast 90. The processing module may then correlate the identified surface location and the distance d to identify the location of the marker 40 within the breast, which may then be added to the model 90' (not shown). For example, the location of the marker 40 and the distal end 24 of the probe 20 may then be used to guide a surgeon during the procedure, e.g., to dissect breast tissue to remove the lesion. Optionally, multiple markers (not shown) may be implanted to surround the lesion and/or define a desired margin or volume, similar to other embodiments herein.

In another option, the probe 20 may include one or more sensors, e.g., a compass, magnetometer, and the like, to provide an orientation of the probe 20, e.g., such that a direction of the distal end 24 into the breast 90 may be determined to facilitate identifying the location of the marker 40 within the breast 90, e.g., to enhance the resulting three-dimensional model 90.'

Figure 15:
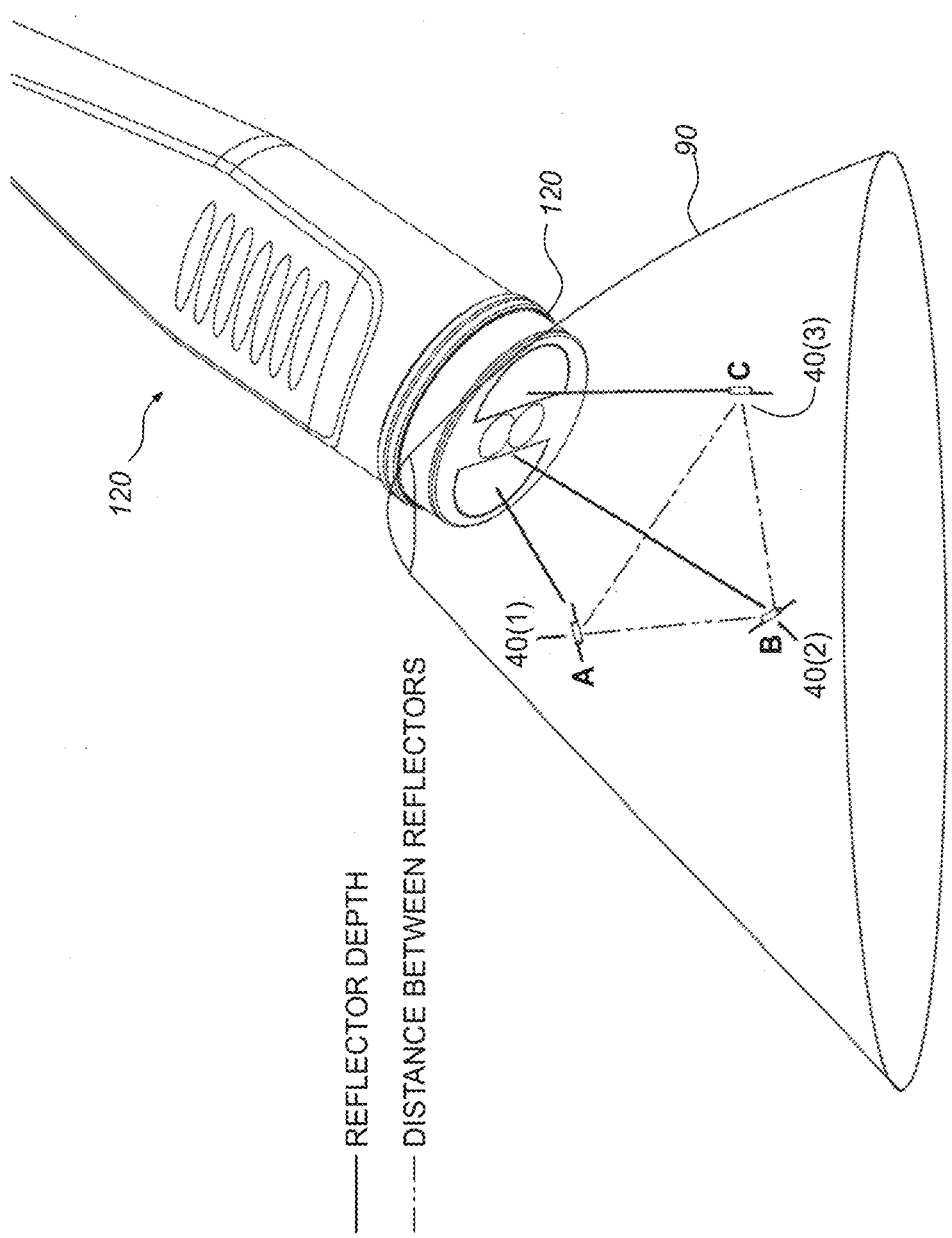
FIG. 15 shows the probe of FIGS. 13A and 13B placed against a patient's breast to obtain a reference frame from a plurality of markers implanted within the breast.

Turning now to FIGS. 13A-15, another exemplary embodiment of a probe 120 is shown that may be used to identify and/or localize one or more markers within a body region, e.g. markers 40 implanted within breast 90 shown in FIG. 15. Generally, the probe 120 includes components similar to other embodiments herein, e.g., including a housing 121 having a distal end 124 including a substrate 132 having a distal surface 132a configured for placement against a body surface, e.g., the patient's skin of the breast 90 shown in FIG. 15 towards the markers 40. The probe also includes an antenna assembly, e.g., including one or more transmit and receive antenna elements on a proximal surface 132b of the substrate 132, and one or more light sources 128, e.g., coupled to a controller and/or display unit (now shown), similar to other embodiments herein.

Unlike previous embodiments, the probe 120 includes a single transmit antenna 132T, e.g., including a pair of bowtie antenna elements, on the proximal surface 132b of the substrate 132, a plurality of receive antennas 132R, each including a pair of bowtie antenna elements, spaced apart from one another on the proximal surface 132b of the substrate 132. Thus, the transmit antenna 132T may be configured for transmitting electromagnetic signals, e.g., ultra-wide band radar signals, into a patient's body along with pulsed light from the light source 128 to cause a switch (not shown) of each marker 40 to open and close to modulate reflected signals from each marker 40. Each receive antenna 132R may be configured for receiving reflected signals from the patient's body independent of the others, and a processor of the probe 120 may process the modulated reflected signals to identify and/or locate each marker 40, e.g., to determine a distance from each marker 40 to the respective receive antennas 132R.

Given that the receive antennas 132R are spaced apart from one another, the distance from each receive antenna 132R to each marker 40 is different and, consequently, the propagation time delay from the transmit signals to the time the receive signals are received by each receive antenna 132R will be different. The processor may use the differences in the time delay and resulting distance dimension to perform trilateration and determine the spatial relationship of each marker 40 relative to the distal end 24, e.g., to determine an x-y-z coordinate location of each marker 40. This spatial relationship may be mapped to a model generated by the system, e.g., similar to other embodiments herein, to allow a surgeon or other user to observe the location of the marker(s) relative to the body region using the model (including representations of each marker) presented on a display.

If multiple markers 40 are implanted within the body region, as shown in FIG. 15, the processor may identify and/or localize each marker simultaneously, e.g., using orthogonal code sequences, or sequentially, e.g., using filters and/or bit commands, similar to other embodiments herein. Alternatively, the probe 120 may be used to identify and localize a single marker implanted within the body region and provide a three-dimensional coordinate for the marker, which may be incorporated into any of the models described herein.

In the embodiment shown in FIG. 14A, the probe 120 includes a transmit antenna 132T located at the center of the substrate 132 and three orthogonally oriented receive antennas 132R positioned evenly around the transmit antenna 132T. Alternatively, as shown in FIG. 14B, a receive antenna 132R' may be mounted at the center with the transmit antenna 132T' with three additional receive antennas 132R' positioned evenly around the central antenna. In a further alternative, shown in FIG. 14C, the probe 120" may include a transmit antenna 132T" located at the center of the substrate 132 "and four orthogonally oriented receive antennas 132R" positioned evenly around the transmit antenna 132T." It will be appreciated that other arrangements may be provided, e.g., including at least two receive antennas spaced apart from one another to provide different propagation time delays and resulting distance measurements to each marker being localized.

Figure 16A:
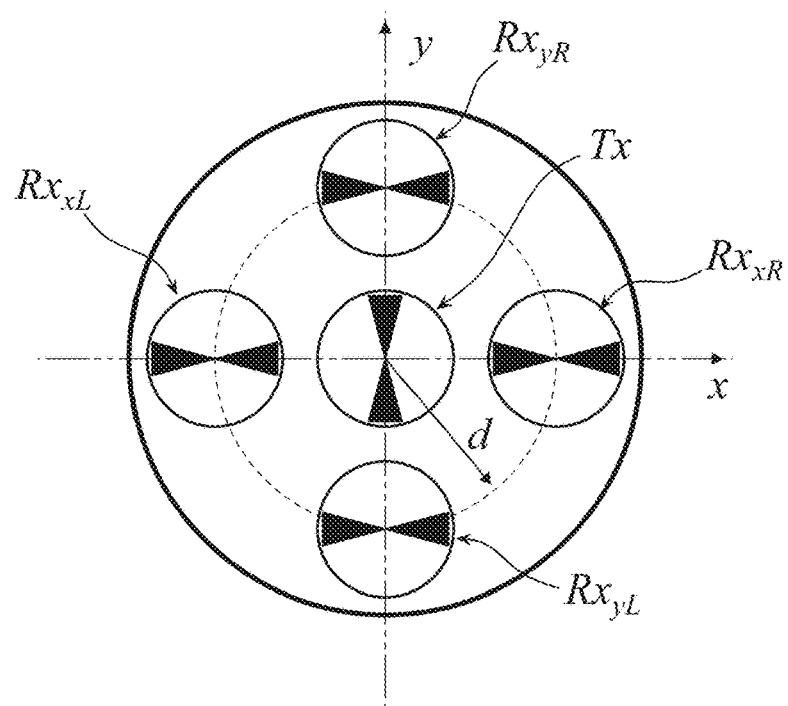
FIGS. 16A-16C show an exemplary method for determining the location of a marker using the probe of FIGS. 13A and 13B.
Figure 16B:
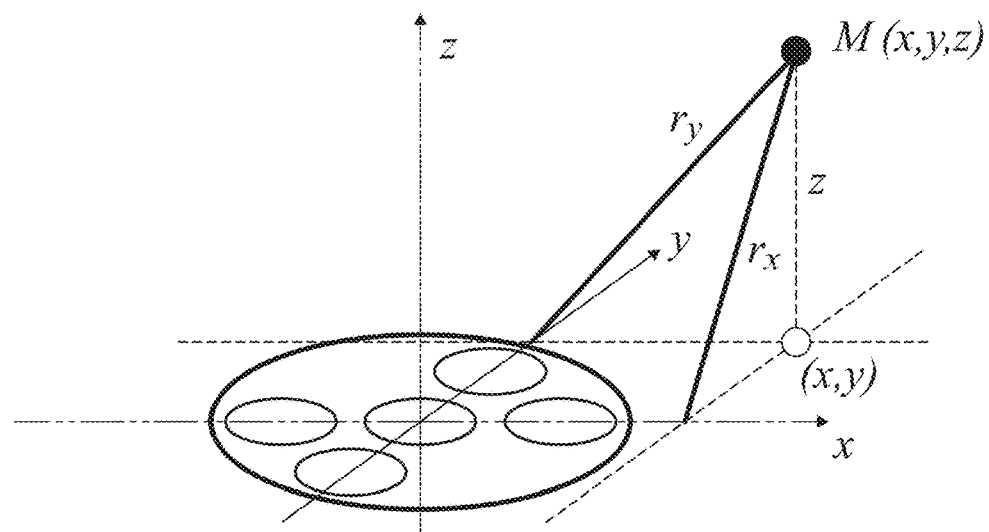
Figure 16C:
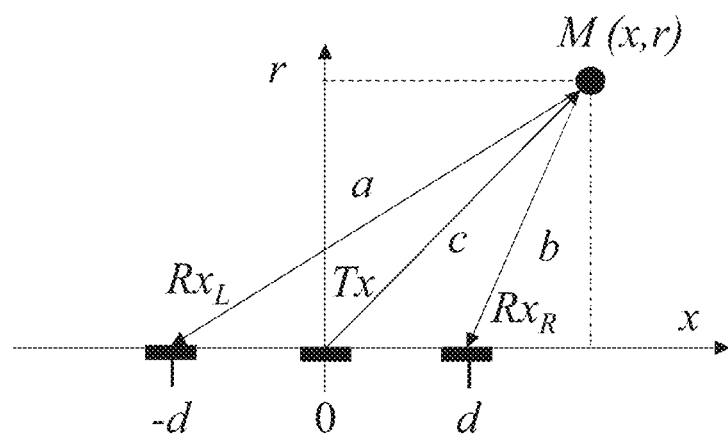
Figure 17:
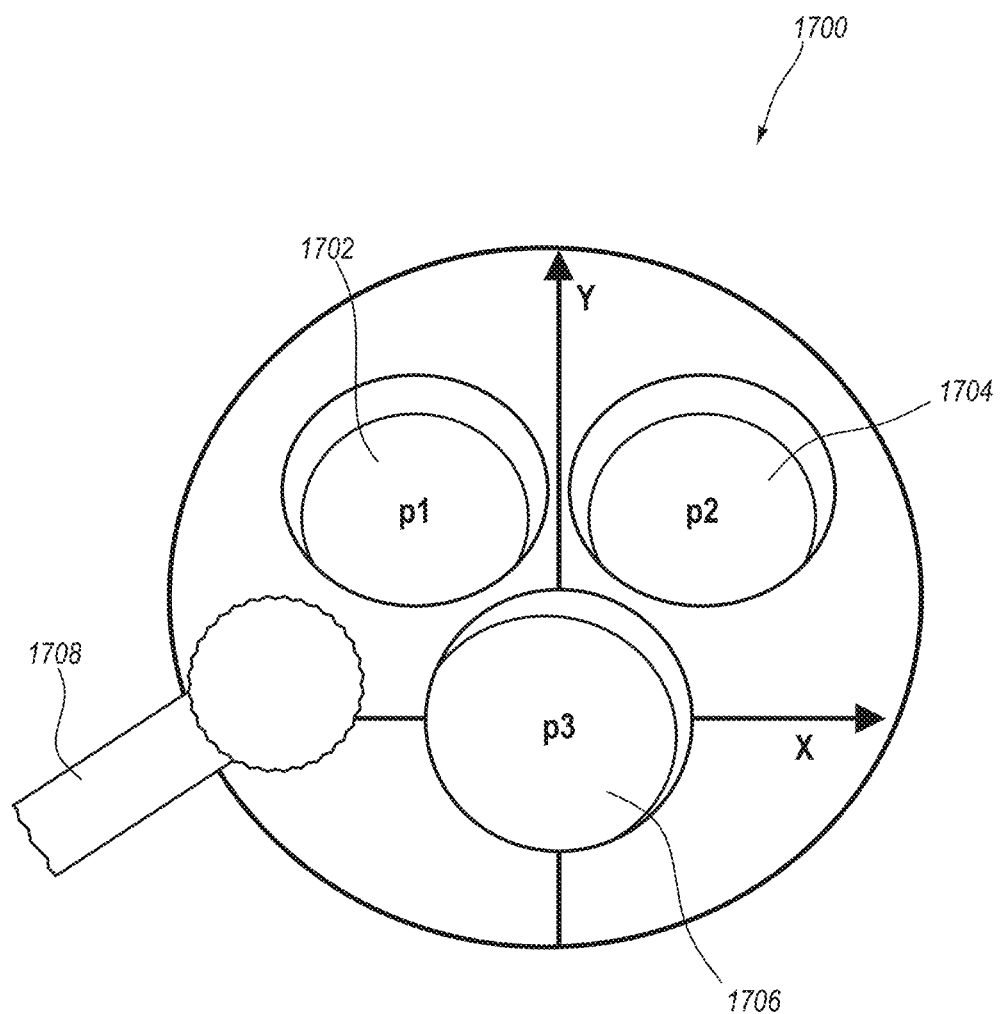
FIG. 17 illustrates an antenna placement template that may be used to coordinate locations of multiple measurements taken by the probe.

Turning to FIGS. 16A-16C, an exemplary method is shown that may be used to determine the three-dimensional location of a marker M relative to a probe including a central transmit antenna Tx, and four receive antennas Rx, spaced apart from the transmit antenna by distance "d", e.g., similar to the configuration of the probe 120" shown in FIG. 14C. In this example, the reference frame used to determine the location of the marker M is centered on the transmit antenna Tx with the x axis aligned with a first pair of the receive antennas $Rx_{xL}$, $Rx_{xR}$, on opposite sides of the transmit antenna $T_x$, and the y axis aligned with an orthogonal second pair of receive antennas $Rx_{yL}$, $Rx_{yR}$, as shown in FIGS. 16A and 16B.

As with other embodiments herein, the transmit antenna $T_x$ may transmit signals, and the receive antennas Rx may receive signals reflected by the marker M (e.g., radar echo), and a processor may analyze the received signals to determine propagation distances for the paths from the transmit antenna Tx to each of the receive antennas Rx. For example, for the receive antennas $Rx_{xL}$, $Rx_{xR}$, the propagation distances $L_x$ and $R_x$ may be determined and for the receive antennas $Rx_{yL}$, $Rx_{yR}$, the propagation distances $L_y$ and $R_y$ may be determined, from the received signals.

As shown in FIG. 16C, the propagation distance L along the x axis corresponds to distances c+a and propagation distance R corresponds to c+b (the propagation distances along the y axis are determined in a similar manner). Given the geometry, the distances a, b, c may be determined as:

$$c = \sqrt{r^2 + x^2}$$

$$a = \sqrt{r^2 + (x+d)^2}$$

$$b = \sqrt{r^2 + (x-d)^2}$$

Thus, the propagation distances can be formulated as:

$$L = c + a = \sqrt{r^2 + x^2} + \sqrt{r^2 + (x+d)^2}$$

$$R = c + b = \sqrt{r^2 + x^2} + \sqrt{r^2 + (x+d)^2}$$

These equations may then be solved for x, $r_x$, y, and $r_y$ resulting in the following sets of equations:

$$x = \frac{(L_x - R_x)(d^2 + L_x R_x)}{2d(L_x + R_x)}$$

$$r_x = \frac{1}{2L}\sqrt{(d^2 - L_x^2)^2 + 4x(d+x)(d^2 - L_x^2)}$$

$$y = \frac{(L_y - R_y)(d^2 + L_y R_y)}{2d(L_y + R_y)}$$

$$r_y = \frac{1}{2L}\sqrt{(d^2 - L_y^2)^2 + 4y(d+y)(d^2 - L_y^2)}$$

Once these values are determined, the z component may be determined using one of the following equations to provide the x, y, z coordinates for the location of the marker M relative to the distal end of the probe. As with other embodiments described elsewhere herein, this spatial relationship may then be presented on a display along with a model of the body region within which the marker M is implanted.

$$z = \sqrt{r_x^2 - y^2}$$

$$z = \sqrt{r_y^2 - x^2}$$

FIGS. 17-20 present another approach for image generation utilizing multiple distance measurements by a single antenna handpiece from a set of locations defined by an antenna placement template 1700. Antenna placement template 1700 illustrates an embodiment wherein three measurement positions may be used to coordinate locations of multiple measurements taken by the probe to generate the model. Methods and devices with additional measurement positions are likewise within the scope of this disclosure. For example, in some embodiments an antenna placement template may have four, five, six, or more antenna placement positions. In order to determine coordinates of the placed markers, the probe may obtain measurements from multiple locations, such as the locations correlating to the positions on the antenna placement template 1700, and the system may use those measurements to calculate the coordinates. If the locations of the measurements are known relative to each other, three or more locations may be used for determining the coordinates of the markers. A positioning rod 1708 may be used to place the antenna placement template 1700.

The antenna placement template 1700 comprises three apertures (i.e., a first aperture 1702, a second aperture 1704, a third aperture 1706) sized to receive a distal end of the probe. Each aperture is positioned at a known location relative to each other aperture. In the illustrated embodiment, the apertures are positioned in a triangular arrangement. The antenna placement template 1700 defines an XY plane for a coordinate system defining the locations of the markers.

The antenna placement template 1700 provides a template to use for measurement locations. A probe with a single receive antenna may be used to take measurements in those three apertures. A localization system may use these measurements to calculate distances and then ultimately generate the coordinates of the each of the reflectors. Subsequently the system may create or display a three-dimensional image of the location of the reflectors. Without the antenna placement template 1700 providing the known locations, a system using a probe with a single antenna would likely need additional points of measurements to determine the coordinates of each of the reflectors.

Figure 18:
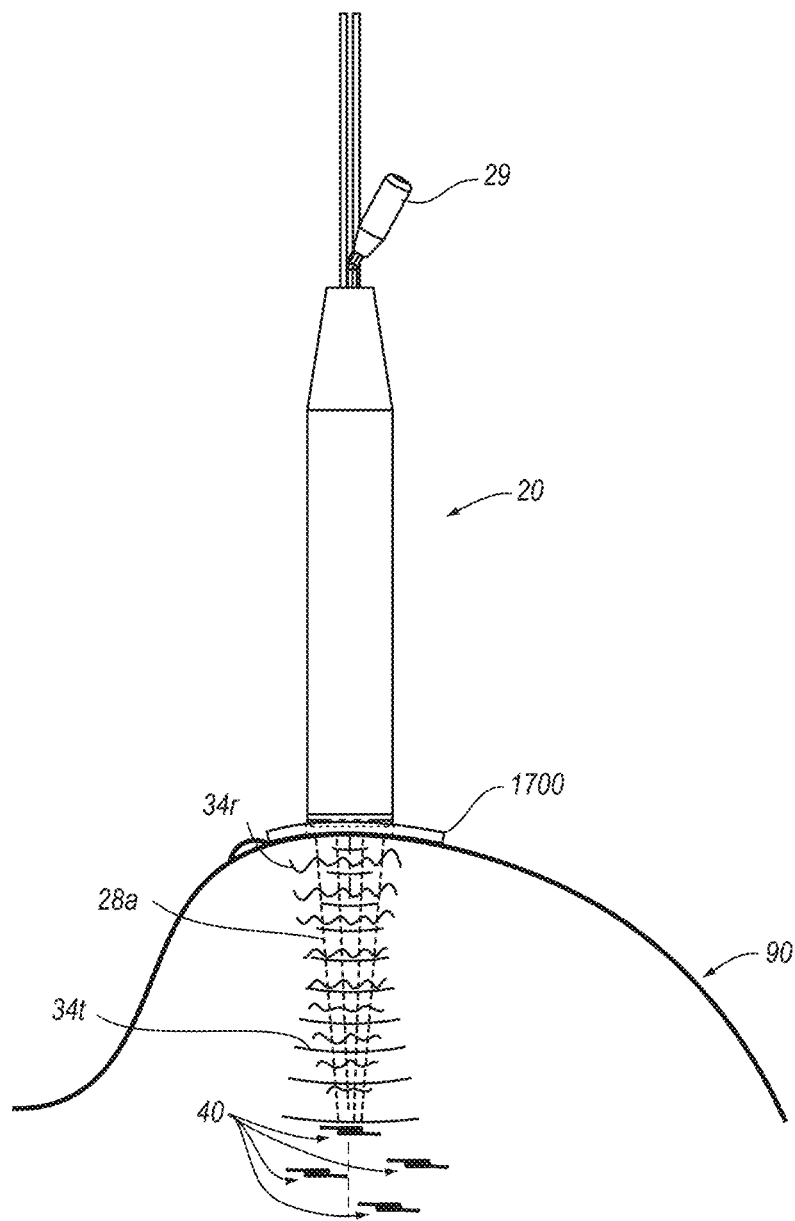
FIG. 18 is a side view of an exemplary embodiment of a probe localizing a plurality of markers implanted within a breast.

FIG. 18 is a side view of an exemplary embodiment of a probe localizing four markers 40 implanted within a breast 90. A physician using the antenna placement template 1700 would place the antenna placement template 800 on a surface of the breast 90. The physician may then sequentially position a distal end of the probe 20 within each aperture of the antenna placement template 800.

While the probe is positioned at each aperture, the probe 20 may transmit electromagnetic signals 34T and transmit light pulses 28a into tissue contacted by the distal end of the probe 90. The probe may receive signals 34R reflected from the markers 40 implanted within the patient's body. The probe 20 may be able to use a single receive antenna to collect measurements at each aperture.

The localization system may use the reflected signals 34R to determine distance values corresponding to distances from each of the plurality of markers to the distal end of the probe 90 positioned at each aperture. For example, the localization system may process a first set of modulated reflected signals from the plurality of markers when probe is placed in the first aperture to determine a first set of distance values corresponding to distances from each of the plurality of markers to the distal end of the probe when in the first aperture. The system may also process a second set of modulated reflected signals from the plurality of markers when probe is placed in the second aperture to determine a second set of distance values corresponding to distances from each of the plurality of markers to the distal end of the probe when in the second aperture. And similarly, the system may process a third set of modulated reflected signals from the plurality of markers when probe is placed in the third aperture to determine a third set of distance values corresponding to distances from each of the plurality of markers to the distal end of the probe when in the third aperture.

In some embodiments, the localization system may transmit electromagnetic signals may be emitted automatically when the probe is placed in an aperture. In some embodiments, a button or switch will be used to initiate the transmission of electromagnetic signals. The localization system may determine coordinates for each of the markers relative to the antenna placement template based on the distance values as illustrated in FIGS. 19-20C.

Figure 19:
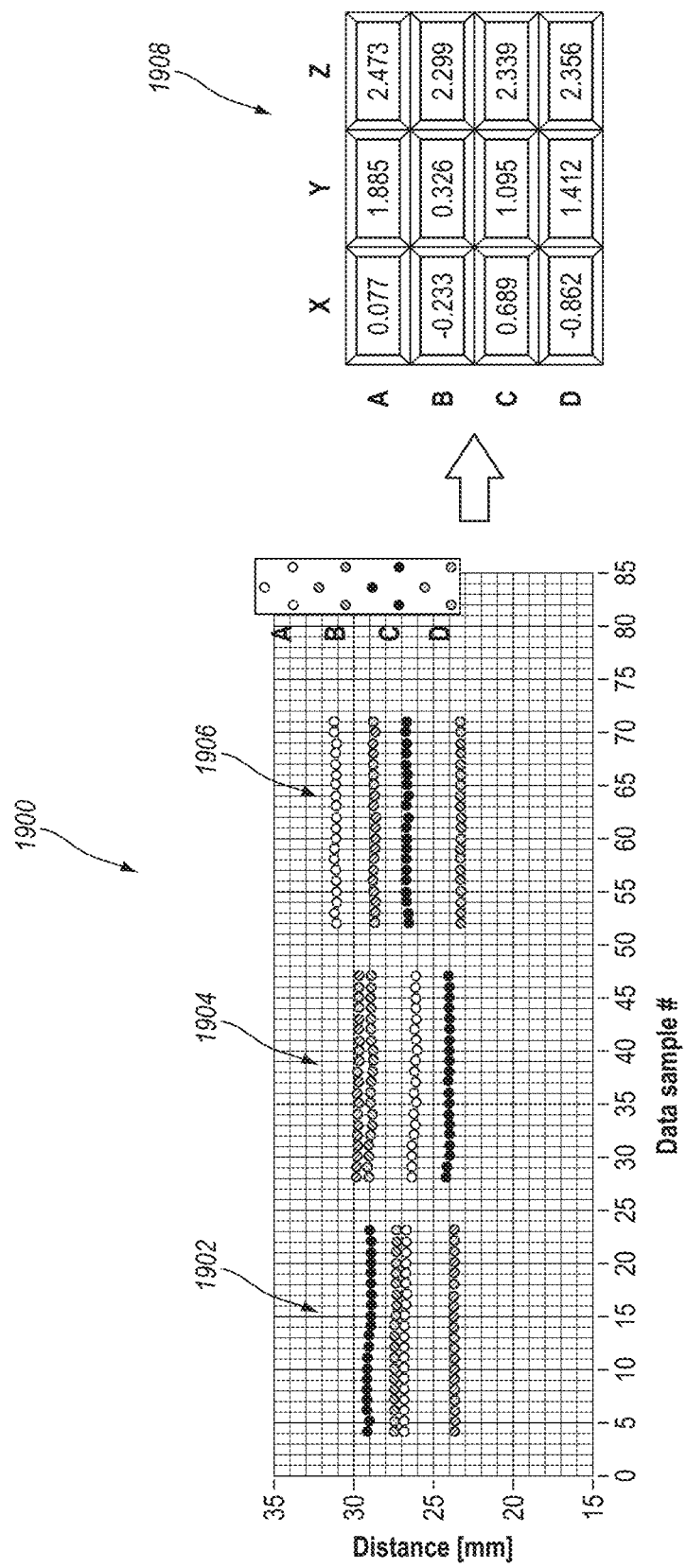
FIG. 19 is a chart with three sets of distance values determined using the probe at locations based on the antenna placement template.

For example, FIG. 19 represents a chart 1900 with three sets of distance values. In this embodiment, there are four markers implanted. Accordingly, each set of distance values includes four groups of samples separated into individual markers. As previously discussed, the localization system may identify these samples because each the markers may include one or more features to facilitate identifying such as unique modulation of the reflected signal.

The samples are obtained sequentially at locations defined by the antenna placement template. In the illustrated embodiment, each set includes multiple distance samples calculated based on the received reflected signals. A first set 1902 of distance values is obtained while the probe is at a first aperture of the antenna placement template. Similarly, a second set 1904 of distance values is obtained while the probe is at a second aperture of the antenna placement template. Additionally, a third set 1906 of distance values is obtained while the probe is at a third aperture of the antenna placement template.

The localization system may use these distance values to calculate the values coordinate table 1908. For example, for the case of a three-position template with equidistant placement, such as antenna placement template 1700 of FIG. 17, the coordinates may be determined using the following equations.

$$x = \frac{d_1^2 - d_2^2}{2L},$$

$$y = \frac{1}{2\sqrt{3}\,L}[2L^2 + 2d_3^2 - (d_2^2 + d_1^2)],$$

$$z = \sqrt{d_3^2 - x^2 - y^2}\,,$$

where L is the distance between the centers of the antenna placements in the template and $d_1$, $d_2$ and $d_3$ are distances measured between the reflector and corresponding antenna location.

Figure 20A:
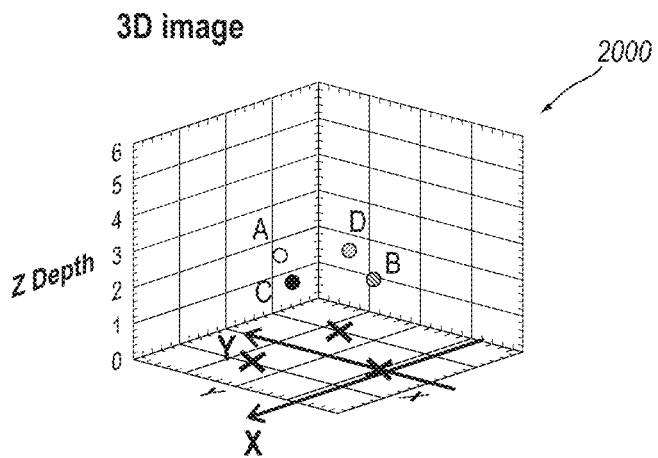
FIG. 20A-20C illustrate potential interfaces that may be used to display the coordinates for each marker.
Figure 20B:
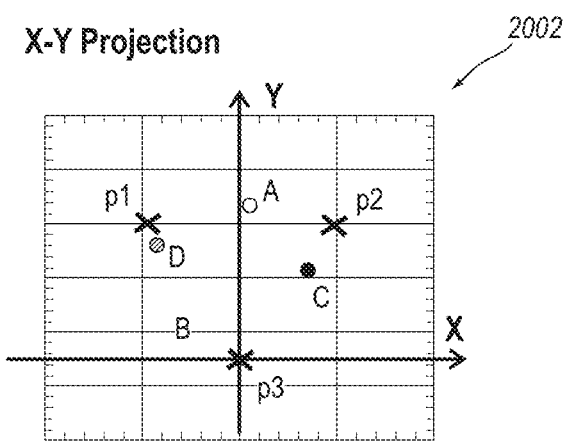
Figure 20C:
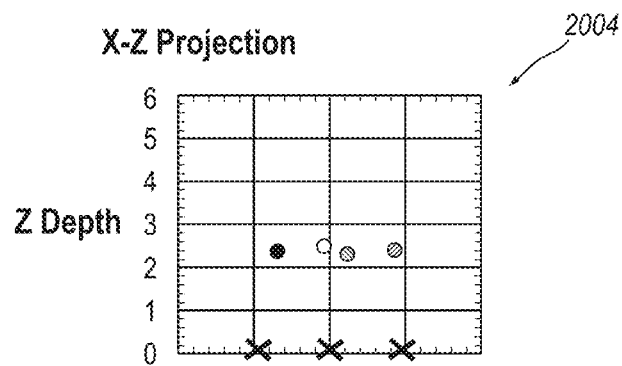

FIGS. 20A-20C illustrate potential interfaces that may be used to display the coordinates for each marker. For example, these interfaces may be shown on the display 38a shown in FIG. 1. The coordinates may be used to show the markers from any angle. The illustrated examples include a perspective view interface 2000, a tope view interface 2002, and a side view interface 2004. These may be shown individually on the display or in combination. The "X" marks identify the location of where the probe took the distance measurements, and the circle marks represent each of the markers.

Additionally, in some embodiments, the localization system may generate a model comprising a three-dimensional representation of the body region showing the markers within the body region. For example, the perspective view interface 2000, the tope view interface 2002, or the side view interface 2004 may be overlaid on a model of the body region.

Additionally, in some embodiments, the localization system may have the ability to track a location of the probe and adjust the orientation of the coordinates based on the probe location. For example, in some embodiments, the probe may include a gyroscope and an accelerometer to track the location and orientation of the probe. As the localization system changes position, the interface displayed may rotate to provide a corresponding view change. Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to an "embodiment" means that a particular feature, structure, or characteristic described in connection with that embodiment is included in at least one embodiment. Thus, references to embodiments throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A system for localization of a region within a patient's body, the system comprising:
    a plurality of markers configured and sized for implantation within a region of a patient's body;
    a probe comprising:
    a transmit antenna for transmitting electromagnetic signals into a patient's body;
    a receive antenna for receiving reflected signals from the plurality of markers configured to be implanted within the patient's body;
    an antenna placement template comprising a plurality of apertures sized to receive a distal end of the probe, each aperture positioned at a known location relative to each other aperture; and
    one or more processors coupled to the probe, the one or more processors configured to:
        process a first set of modulated reflected signals from the plurality of markers when the probe is placed in a first aperture of the plurality of apertures to determine a first set of distance values corresponding to distances from each of the plurality of markers to the distal end of the probe when in the first aperture;
        process a second set of modulated reflected signals from the plurality of markers when the probe is placed in a second aperture of the plurality of apertures to determine a second set of distance values corresponding to distances from each of the plurality of markers to the distal end of the probe when in the second aperture;
        process a third set of modulated reflected signals from the plurality of markers when the probe is placed in a third aperture of the plurality of apertures to determine a third set of distance values corresponding to distances from each of the plurality of markers to the distal end of the probe when in the third aperture;
        determine three-dimensional coordinates for each of the plurality of markers relative to the antenna placement template using trilateration based on the first set of distance values, the second set of distance values, and the third set of distance values and a distance between centers of the plurality of apertures.

2. The system of claim 1, further comprising a display in communication with the one or more processors, the display to present an image of the plurality of markers using the three-dimensional coordinates.

3. The system of claim 2, wherein the one or more processors are further configured to generate a model, wherein the model comprises a three-dimensional representation of the region of the patient's body showing the plurality of markers within the region of the patient's body, and wherein the display is configured to present the model.

4. The system of claim 1, wherein the antenna placement template comprises three apertures.

5. The system of claim 1, wherein each of the plurality of markers comprises:
    an energy converter configured to transform light pulses into electrical energy;
    one or more elongate members coupled to a switch to provide one or more antennas; and
    a circuit coupled to the energy converter and the switch to open and close the switch to modulate electromagnetic signals reflected by the marker based at least in part on the light pulses.

6. The system of claim 5, wherein the probe further comprises a light source for delivering the light pulses into the patient's body.

7. The system of claim 6, wherein the one or more processors are further configured to identify each of the plurality of markers based on modulation of the reflected electromagnetic signals.

8. The system of claim 5, wherein the electromagnetic signals comprise a plurality of ultrawide band radar pulses generated in synchronization with the light pulses.

9. The system of claim 1, wherein the transmit antenna is a bowtie antenna and the receive antenna is a bowtie antenna that together form a single Maltese cross antenna.

10. The system of claim 1, further comprising a display in communication with the one or more processors, the display to present output elements associated with each of the plurality of markers, wherein the output elements represent current distances from the probe to the plurality of markers based on the three dimensional coordinates of the plurality of markers and a current location of the probe, wherein each of the output elements are different colors.

* * * * *